US009568483B2

(12) United States Patent
Rubin et al.

(10) Patent No.: US 9,568,483 B2
(45) Date of Patent: Feb. 14, 2017

(54) MOLECULAR SUBTYPING, PROGNOSIS AND TREATMENT OF PROSTATE CANCER

(75) Inventors: Mark A. Rubin, New York, NY (US); Himisha Beltran, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 0 days.

(21) Appl. No.: 14/112,358

(22) PCT Filed: Mar. 28, 2012

(86) PCT No.: PCT/US2012/030836
§ 371 (c)(1),
(2), (4) Date: Oct. 17, 2013

(87) PCT Pub. No.: WO2012/145129
PCT Pub. Date: Oct. 26, 2012

(65) Prior Publication Data
US 2014/0037647 A1 Feb. 6, 2014

Related U.S. Application Data

(60) Provisional application No. 61/476,628, filed on Apr. 18, 2011, provisional application No. 61/490,441, filed on May 26, 2011, provisional application No. 61/544,905, filed on Oct. 7, 2011.

(51) Int. Cl.
C12Q 1/68 (2006.01)
C07H 21/04 (2006.01)
G01N 33/68 (2006.01)
G01N 33/574 (2006.01)
A61K 31/00 (2006.01)
A61K 31/437 (2006.01)
A61K 31/444 (2006.01)
A61K 31/496 (2006.01)
A61K 31/506 (2006.01)
A61K 31/519 (2006.01)
A61K 31/5377 (2006.01)
A61K 31/55 (2006.01)
A61K 31/675 (2006.01)
A61K 31/713 (2006.01)

(52) U.S. Cl.
CPC ........... G01N 33/6893 (2013.01); A61K 31/00 (2013.01); A61K 31/437 (2013.01); A61K 31/444 (2013.01); A61K 31/496 (2013.01); A61K 31/506 (2013.01); A61K 31/519 (2013.01); A61K 31/5377 (2013.01); A61K 31/55 (2013.01); A61K 31/675 (2013.01); A61K 31/713 (2013.01); C12Q 1/6886 (2013.01); G01N 33/57434 (2013.01); C12Q 2600/112 (2013.01); C12Q 2600/156 (2013.01); C12Q 2600/158 (2013.01); G01N 2333/82 (2013.01); G01N 2333/91215 (2013.01)

(58) Field of Classification Search
CPC .... A61K 31/00; A61K 31/437; A61K 31/444; A61K 31/496; A61K 31/506; A61K 31/519; A61K 31/5377; A61K 31/55; A61K 31/675; A61K 31/713; C12Q 1/6886; C12Q 2600/158; C12Q 2600/118; C12Q 2600/106; C12Q 2600/112; C12Q 2600/136; C12Q 1/6883; C12Q 2600/156; C12Q 2600/178; C12Q 1/6813; C12Q 1/6851; C12Q 1/485; C12Q 2545/101; G01N 2333/82; G01N 2333/91215; G01N 33/57434
See application file for complete search history.

(56) References Cited

U.S. PATENT DOCUMENTS

| 2003/0224464 | A1* | 12/2003 | Thompson | 435/7.23 |
|---|---|---|---|---|
| 2007/0128639 | A1* | 6/2007 | Chinnaiyan et al. | 435/6 |
| 2007/0212702 | A1 | 9/2007 | Tomlins et al. | |
| 2009/0036415 | A1* | 2/2009 | Rubin et al. | 514/182 |
| 2010/0196902 | A1 | 8/2010 | Pestano et al. | |
| 2010/0196907 | A1* | 8/2010 | Semizarov | C12Q 1/6886 435/6.18 |

FOREIGN PATENT DOCUMENTS

WO 2009/045443 A2 4/2009
WO 2010/135411 A2 11/2010

OTHER PUBLICATIONS

Kela et al. The Prostate 2009 vol. 69 pp. 1034-1044.*
Zhou (Nature Genetics 1998 vol. 20 pp. 189-193).*
Zhao (Cancer Research 2004 vol. 64 pp. 3060-3071).*
Edwards (Clin Cancer Res 2003 vol. 9 pp. 5271-5281).*
Koivisto (Cancer Research 1997 vol. 57 pp. 314-319).*
Sen (Journal of the National Cancer Institute 2002 vol. 94 No. 17 pp. 1320-1329).*
Tanner (Clincal Cancer Research 2000 vol. 6 pp. 1833-1839).*
Sakakura (British Journal of Cancer 2001 vol. 84(6) pp. 824-831).*
Haverty (BMC Medical Genomics vol. 2(21) pp. 1-15 May 6, 2009).*

(Continued)

Primary Examiner — Amanda Haney
(74) Attorney, Agent, or Firm — Scully Scott Murphy & Presser

(57) ABSTRACT

Disclosed herein are new prognostic molecular markers for prostate cancer. More specifically, the invention has identified that overexpression or amplification of at least one of AURKA or MYCN define a distinct subgroup of prostate cancer that is predisposed to the development of lethal NEPC, who will benefit from early intervention.

9 Claims, 21 Drawing Sheets
(16 of 21 Drawing Sheet(s) Filed in Color)

(56) References Cited

OTHER PUBLICATIONS

Beltran et al. Journal of Clincial Oncology 2011 Genitourinary Cancers Symposium vol. 29 No. 7 suppl (Mar. 1 supplement), 2011:19.*

Beltran et al. Proceedings: AACR 102$^{nd}$ Annual Meeting Apr. 2-6, 2011; Orland FL. Meeting Abstract published in Cancer Res 2011; 71(8 Suppl) Abstract nr957.*

Beltran, H. et al., "Molecular Characterization of Neuroendocrine Prostate Cancer and Identification of New Drug Targets" Cancer Discovery (Nov. 2011) pp. 487-495, vol. 1.

Berger, M.F. et al., The genomic complexity of primary human prostate cancer Nature (Feb. 10, 2011) pp. 214-220, vol. 470.

Brawn, P.N. et al., "The dedifferentiation of metastatic prostate carcinoma" Br. J. Cancer (1989) pp. 85-88, vol. 59.

Carney, D.N. et al., "Establishment and Identification of Small Cell Lung Cancer Cell Lines Having Classic and Variant Features" Cancer Research (Jun. 1985) pp. 2913-2923, vol. 45.

Cheung, C.H.A. et al., "Aurora kinase inhibitors in preclinical and clinical testing" Expert Opin. Investig. Drugs (2009) pp. 379-398, vol. 18, No. 4.

Jemal, A. et al., "Global Cancer Statistics" CA Cancer J. Clin. (Mar./Apr. 2011) pp. 69-90, vol. 61, No. 2.

Habegger, L. et al., "RSEQtools: a modular framework to analyze RNA-Seq data using compact, anonymized data summaries" Bioinformatics (2011) pp. 281-283, vol. 27, No. 2.

Hsu, J.Y. et al., "Mitotic Phosphorylation of Histone H3 Is Governed by Ipl1/aurora Kinase and Glc7/PP1 Phosphatase in Budding Yeast and Nematodes" Cell (Aug. 4, 2000) pp. 279-297, vol. 102.

Lee, E.C.Y. et al., "Targeting Aurora Kinases for the Treatment of Prostate" Cancer Research (May 15, 2006) pp. 4996-5002, vol. 66, No. 10.

Lotan, T.L. et al., "ERG gene rearrangements are common in prostatic small cell carcinomas" Modern Pathology (2011) pp. 820-828, vol. 24.

Mortazavi, A. et al., "Mapping and Quantifying Mammalian Transcriptomes by RNA-Seq" Nature Methods (Jul. 2008) pp. 621-628, vol. 5, No. 7.

Mosquera, J.M. et al., "Prevalence of TMPRSS2-ERG Fusion Prostate Cancer among Men Undergoing Prostate Biopsy in the United States" Clinical Cancer Research (Jul. 15, 2009) pp. 4706-4711, vol. 15, No. 14.

Otto, T. et al., "Stabilization of N-Myc Is a Critical Function of Aurora A in Human Neuroblastoma" Cancer Cell (Jan. 6, 2009) pp. 67-78, vol. 15.

Palmgren, J.S. et al., "Unusual and Underappreciated: Small Cell Carcinoma of the Prostate" Seminars in Oncology (2007) pp. 22-29, vol. 34.

Park, K. et al., "Antibody-Based Detection of ERG Rearrangement—Positive Prostate Cancer" NEO Plasia (Jul. 2010) pp. 590-598, vol. 12, No. 7.

Perner, S. et al., "TMPRSS2:ERG Fusion-Associated Deletions Provide Insight into the Heterogeneity of Prostate Cancer" Cancer Research (Sep. 1, 2006) pp. 8337-8341, vol. 66, No. 17.

Pflueger, D. et al., "Discovery of non-ETS gene fusions in human prostate cancer using next-generation RNA sequencing" Genome Research (2011) pp. 56-67, vol. 21.

Ponomarev, V. et al., "A novel triple-modality reporter gene for whole-body fluorescent, bioluminescent, and nuclear noninvasive imaging" European Journal of Nuclear Medicine and Molecular Imaging (May 2004) pp. 740-751, vol. 31, No. 5.

Quail, M.A. et al., "A large genome centre's improvements to the Illumina sequencing system" Nat Methods. (Dec. 2008) pp. 1005-1010, vol. 5, No. 12.

Rickman, D.S. et al., "SLC45A3-ELK4 Is a Novel and Frequent Erythroblast Transformation-Specific Fusion Transcript in Prostate Cancer" Cancer Research (Apr. 1, 2009) pp. 2734-2738, vol. 69, No. 7.

Rickman, D.S. et al., "ERG Cooperates with Androgen Receptor in Regulating Trefoil Factor 3 in Prostate Cancer Disease Progression" Neoplasia (Dec. 2010) pp. 1031-1040, vol. 12, No. 12.

Scheble, V.J. et al., "ERG rearrangement is specific to prostate cancer and does not occur in any other common tumor" Modern Pathology (2010) pp. 1061-1067, vol. 23.

Setlur, S.R. et al., "Estrogen-Dependent Signaling in a Molecularly Distinct Subclass of Aggressive Prostate Cancer" J Natl Cancer Inst (2008) pp. 815-825, vol. 100.

Slack, A. et al., "The p53 regulatory gene MDM2 is a direct transcriptional target of MYCN in neuroblastoma" PNAS (Jan. 18, 2005) pp. 731-736, vol. 102, No. 3.

Strieder, V. et al., "Regulation of N-myc expression in development and disease" Cancer Letters (2002) pp. 107-119, vol. 180.

Tomlins, S.A. et al., "Recurrent Fusion of TMPRSS2 and ETS Transcription Factor Genes in Prostate Cancer" Science (Oct. 28, 2005) pp. 644 , vol. 310.

Tung, W.L. et al., "Use of Irinotecan for Treatment of Small Cell Carcinoma of the Prostate" The Prostate (2011) pp. 675-681, vol. 71.

Van Bokhoven, A. et al., "Molecular Characterization of Human Prostate Carcinoma Cell Lines" The Prostate (2003) pp. 205-225, vol. 57.

Varambally, S. et al., "The polycomb group protein EZH2 is involved in progression of prostate cancer" Nature (Oct. 10, 2002) pp. 624-629, vol. 419.

Wang, W. et al., "Small Cell Carcinoma of the Prostate A Morphologic and Immunohistochemical Study of 95 Cases" Am J Surg Pathol (Jan. 2008) pp. 65-71, vol. 32, No. 1.

Williamson, S.R. et al., "ERG-TMPRSS2 rearrangement is shared by concurrent prostatic adenocarcinoma and prostatic small cell carcinoma and absent in small cell carcinoma of the urinary bladder: evidence supporting monoclonal origin" Modern Pathology (2011) pp. 1120-1127, vol. 24.

Wu, A. et al., "Transposon-based interferon gamma gene transfer overcomes limitations of episomal plasmid for immunogene therapy of glioblastoma" Cancer Gene Therapy (2007) pp. 550-560, vol. 14.

Yang, D. et al., "Therapeutic potential of a synthetic lethal interaction between the MYC proto-oncogene and inhibition of aurora-B kinase" PNAS (Aug. 3, 2010) pp. 13836-13841, vol. 107, No. 31.

Zhou, H. et al., "Tumour amplified kinase STK15/BTAK induces centrosome amplification, aneuploidy and transformation" Nature Genetics (Oct. 1998) pp. 189-193, vol. 20.

Myllykangas, S., et al., "Specificity selection and significance of gene amplifications in cancer", Seminars in Cancer Biology, vol. 17, No. 1, Jan. 10, 2007, pp. 42-55.

Extended European Search Report received in related EP 12773580.1 dated Nov. 10, 2014.

* cited by examiner

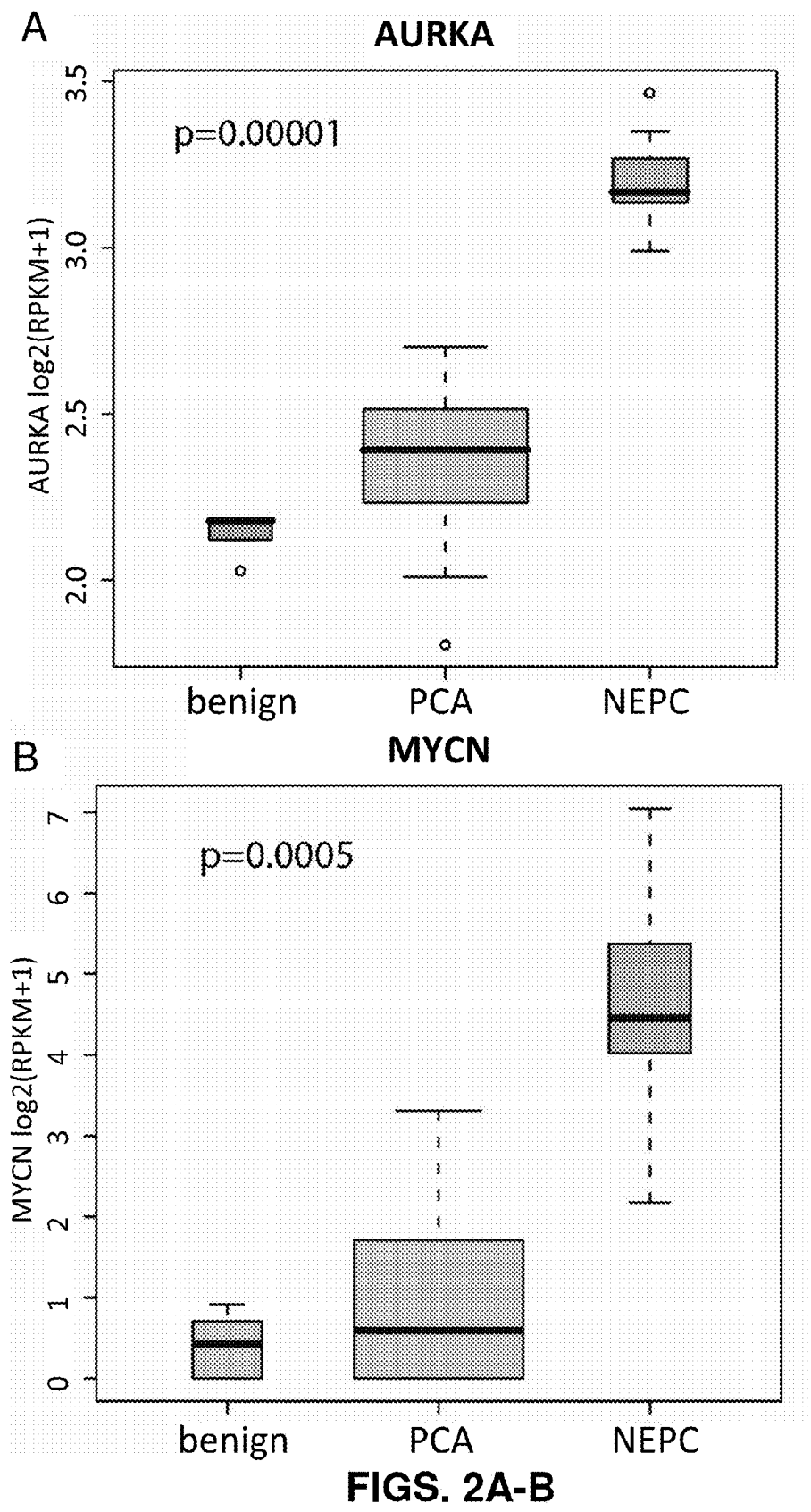
FIGS. 2A-B

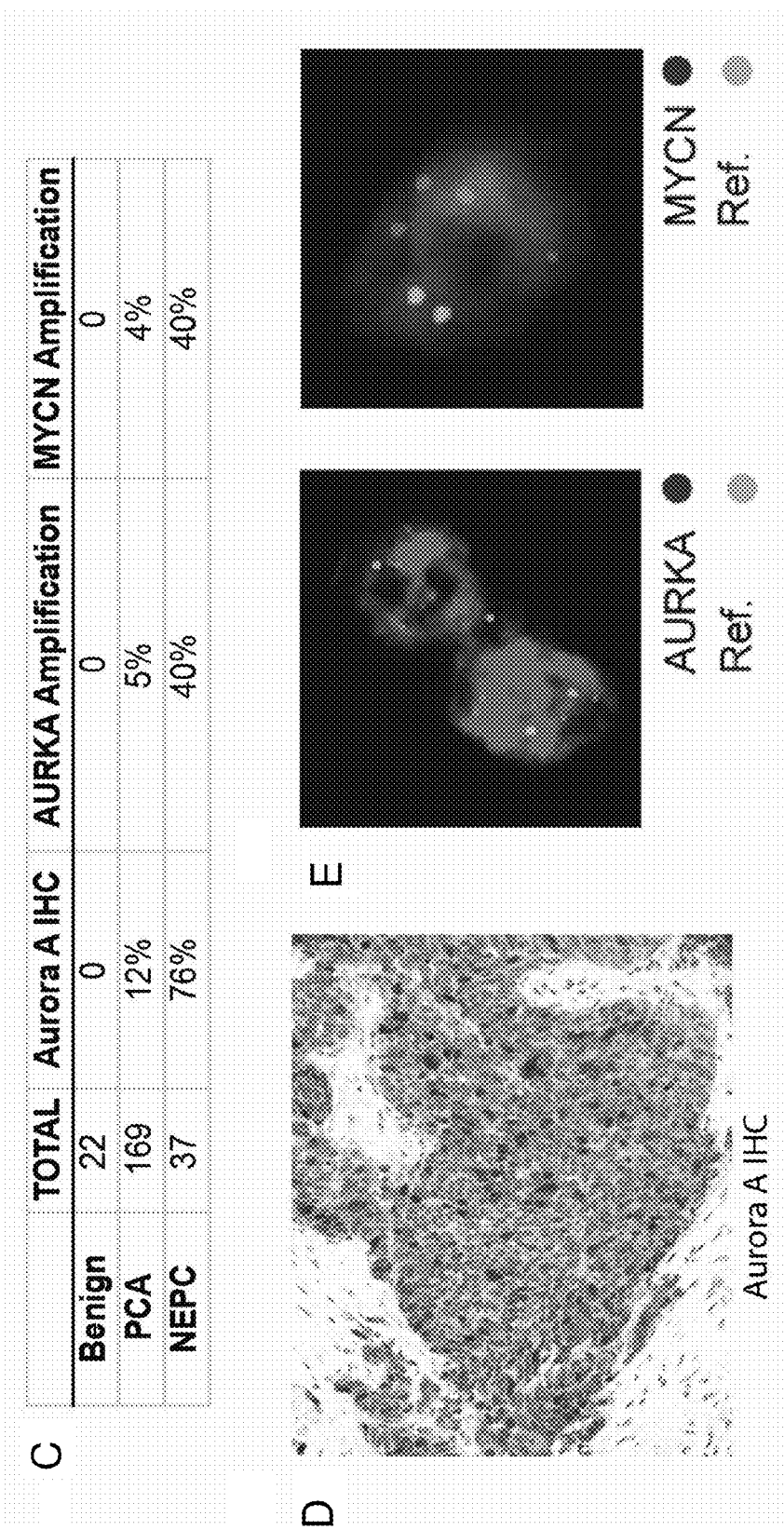
FIGS. 2C-E

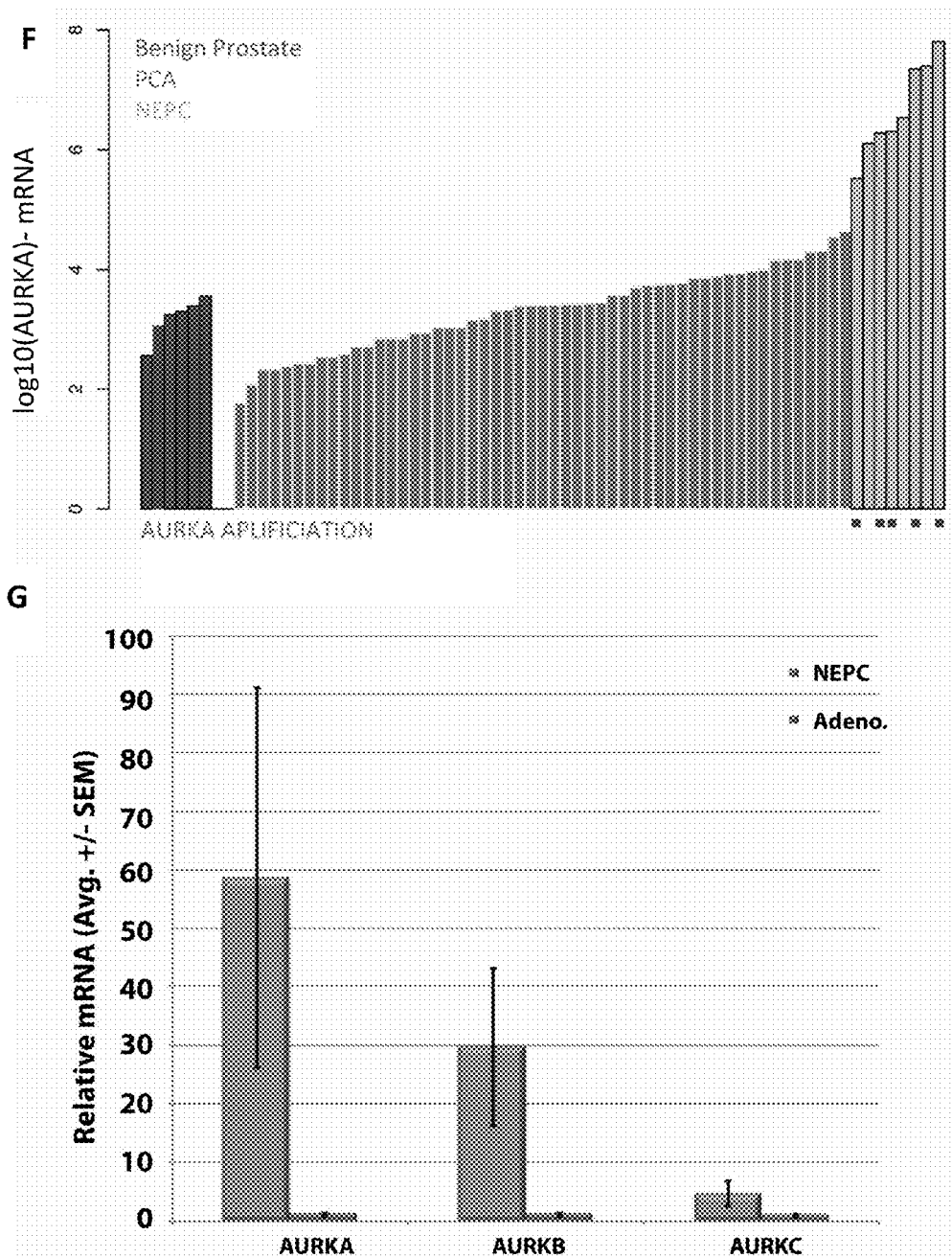
FIGS. 2F-G

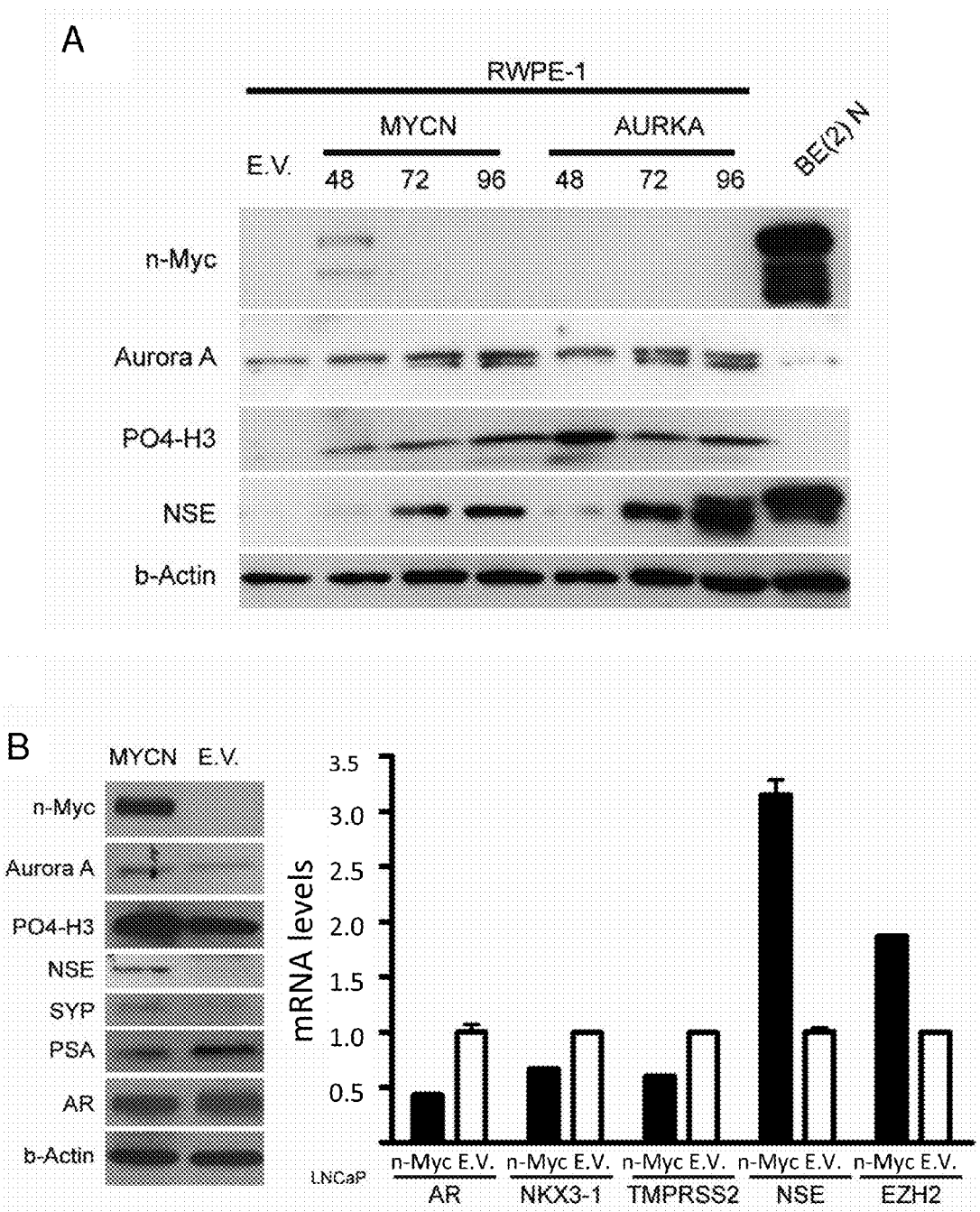
FIGS. 3A-B

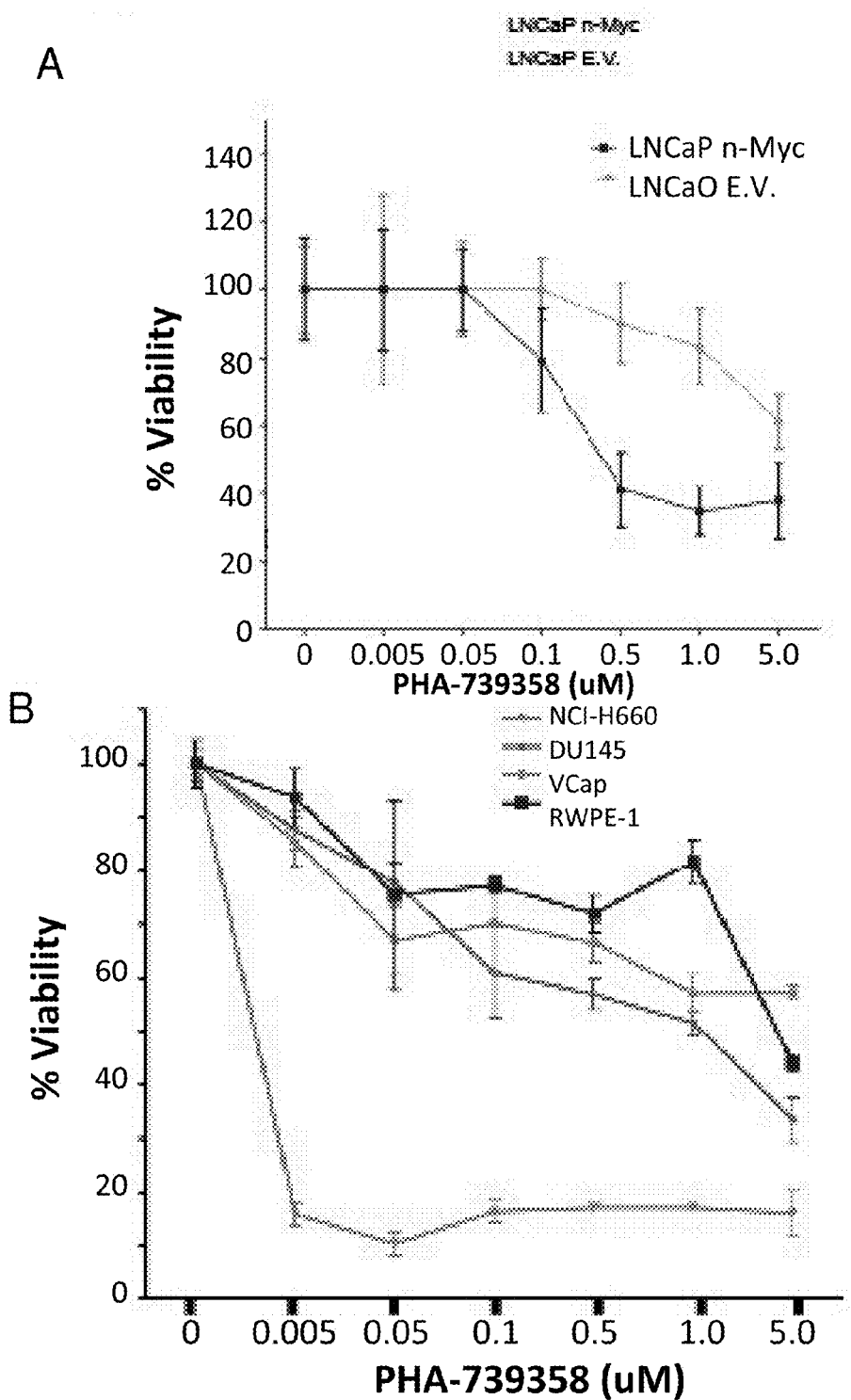
FIGS. 4A-B

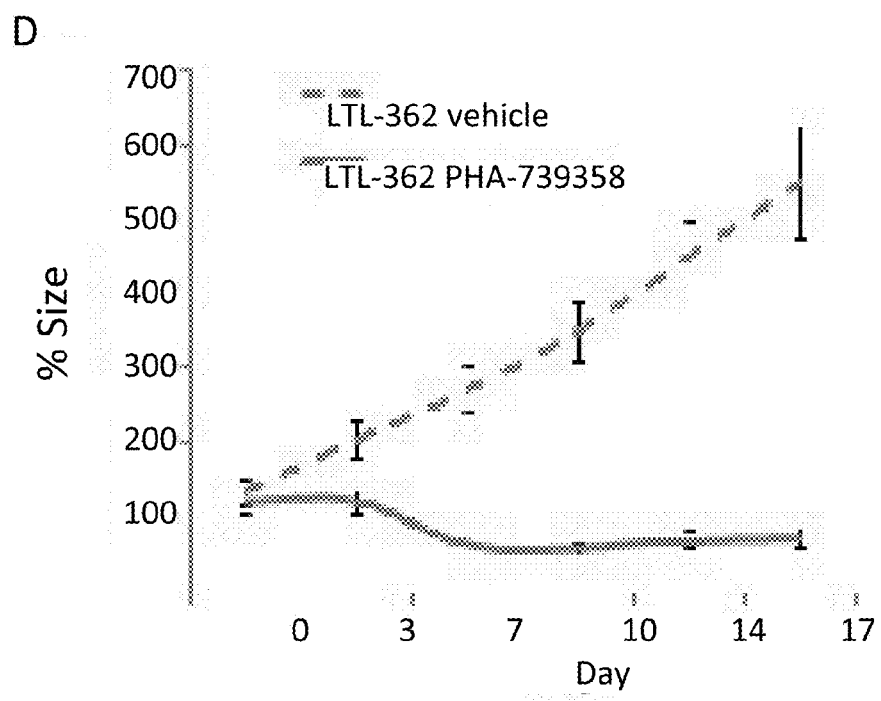
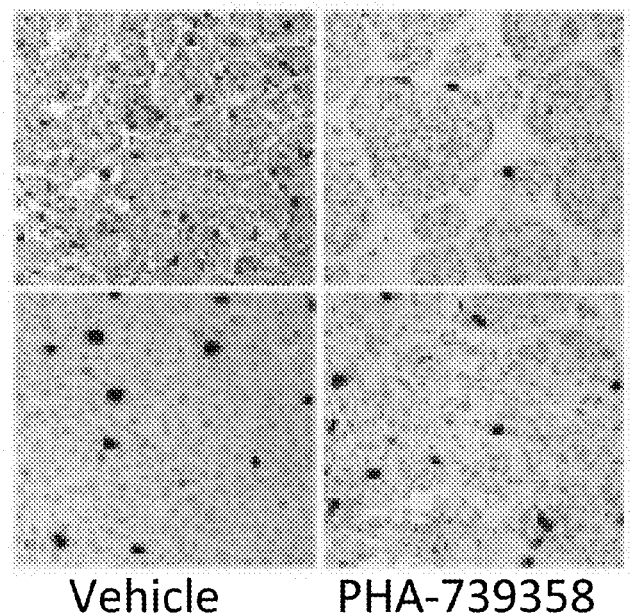
FIGS. 4D-E

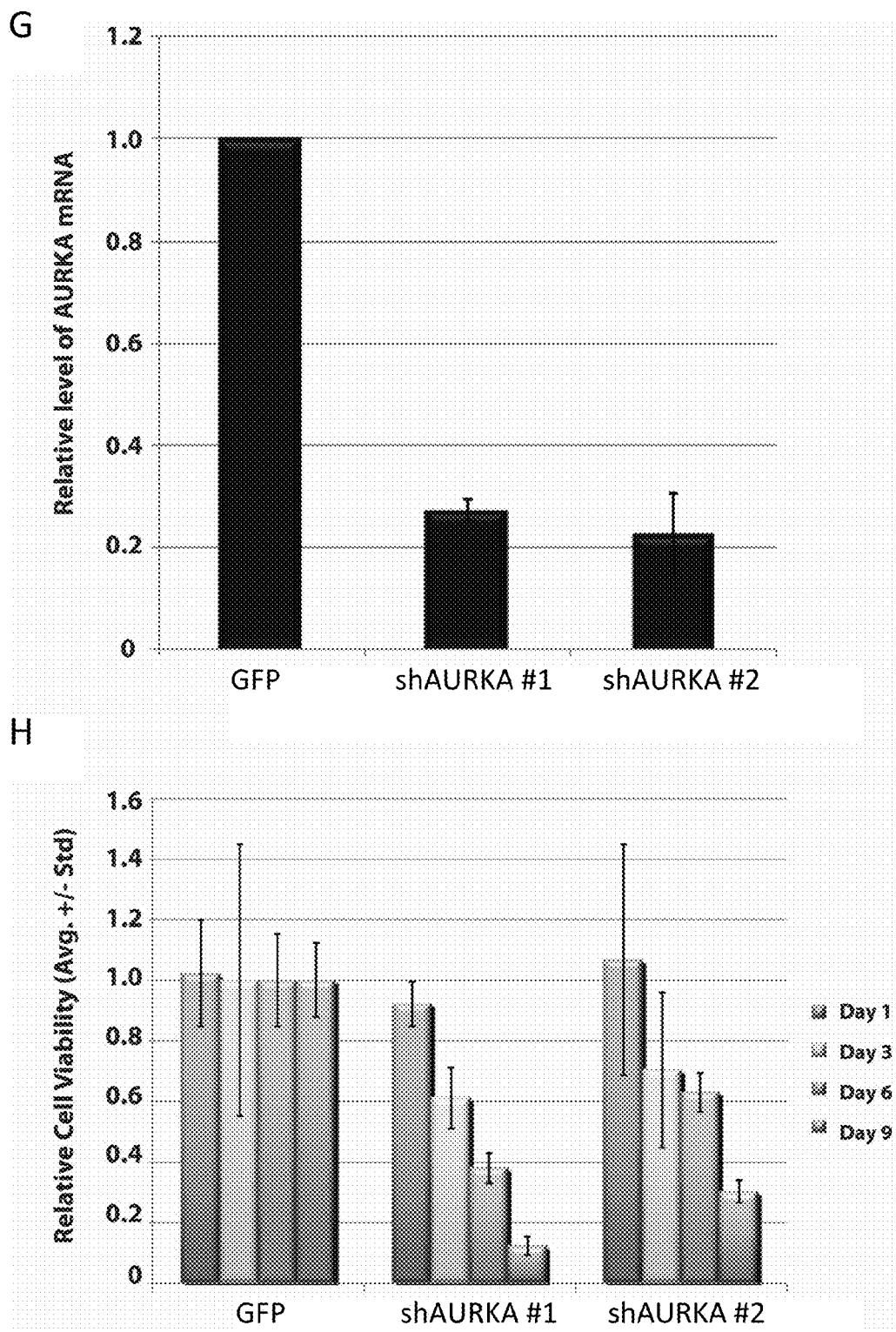
FIGS. 4G-H

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
gccctgtctt actgtcattc g                                     21

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
agagagtggt cctcctggaa g                                     21

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 3
ctgggaactg tgttggag                                                    18

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
cgactgaggg cttctttc                                                    18

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
ctggctaaat acaaccagct ca                                               22

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
cacagcacac tgggattacg                                                  20

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 7
cagtggattc gcgggcacag a                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
aaggtgaagg ggcaggacgg g                                                21

<210> SEQ ID NO 9
<211> LENGTH: 24
<212> TYPE: DNA
<213> ORGANISM: Artificial Sequence
<220> FEATURE:
<223> OTHER INFORMATION: Synthetic Oligonucleotide

```
<400> SEQUENCE: 9
ttgtgttttc ccaacgcata ttcc                                          24

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
agcgggttgt accacagtct c                                             21

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
cctgggctgt tccaacgag                                                19

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
gctctgtcca cggtgctg                                                 18

<210> SEQ ID NO 13
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 13
cggtcctctg ggcagtgtg                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
agccgccttc gcaagtctc                                                19

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
ccgccgccac tgccactc                                                 18

<210> SEQ ID NO 16
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gggcttcacc tcgggactgc                                                   20
```

MOLECULAR SUBTYPING, PROGNOSIS AND TREATMENT OF PROSTATE CANCER

CROSS REFERENCE TO RELATED APPLICATIONS

This application claims priority from U.S. Provisional Application No. 61/476,628, filed Apr. 18, 2011, U.S. Provisional Application No. 61/490,441, filed May 26, 2011, and U.S. Provisional Application No. 61/544,905, filed Oct. 7, 2011, the entire contents of each of which are incorporated herein by reference.

STATEMENT REGARDING FEDERALLY SPONSORED RESEARCH OR DEVELOPMENT

This invention was made with Government Support under Contract No. U01CA111275, NCI EDRN (National Cancer Institute, Early Detection Research Network). The Government has certain rights in this invention.

FIELD OF THE DISCLOSURE

This invention relates to cancer prognosis and treatment, particularly prognosis and treatment of prostate cancer based on molecular subtyping.

INCORPORATION BY REFERENCE OF SEQUENCE LISTING

The Sequence Listing in an ASCII text file, named as 27558_5019_05_SequenceListing.txt of 4 KB, created on Oct. 16, 2013, and submitted to the United States Patent and Trademark Office via EFS-Web, is incorporated herein by reference.

BACKGROUND ART

Neuroendocrine prostate cancer (NEPC) is an aggressive subtype of prostate cancer that can arise de novo, but much more commonly arises after hormonal therapy for prostate adenocarcinoma (PCA) (PALMGREN et al., Semin Oncol., 34:22-9 (2007)). It is known that the amount of neuroendocrine differentiation increases with disease progression and correlates with patient exposure to long-term androgen deprivation therapy. NEPC reportedly differs histologically from PCA, and is characterized by the presence of small round blue neuroendocrine cells, which do not express androgen receptor (AR) or secrete prostate specific antigen (PSA), but usually express neureondocrine markers such as chromogranin A, synaptophysin, and neuron specific enolase (NSE)(WANG et al., Am J Surg Pathol., 32:65-71 (2008)). The prostate cancer specific TMPRSS2-ERG gene rearrangement (TOMLINS et al., Science, 310:644-8 (2005)) has been reported in approximately 50% of NEPC (LOTAN et al., Mod Pathol. (2011)), similar to the frequency in PCA (MOSQUERA et al., Clin Cancer Res., 15:4706-11 (2009)). This suggests clonal origin of NEPC from PCA and distinguishes NEPC from small carcinomas of other primary sites LOTAN et al., Mod Pathol. (2011), SCHEBLE et al., Mod Pathol., 23:1061-7 (2010), WILLIAMSON et al., Mod Pathol. (2011)). The poor molecular characterization of NEPC accounts in part for the lack of disease specific therapeutics.

The development of treatment related neuroendocrine prostate cancer (t-NEPC, also referred to as anaplastic prostate cancer) is thought to drive approximately 25% of the nearly 34,000 cases/year of lethal prostate cancer in the United States (Jemal et al., CA Cancer J. Clin 61(2): 69-90, 2011). However, because t-NEPC is under-recognized and patients are rarely biopsied to make the diagnosis, this number may actually be higher. Data from autopsy studies suggests that the incidence of t-NEPC may be significantly underestimated (Brawn and Speights, Br J Cancer 59(1): 85-88, 1989). With the introduction of new highly potent androgen receptor (AR)-targeted therapies into the clinic, the incidence of t-NEPC will likely escalate. Patients who develop t-NEPC have an aggressive clinical course, often develop visceral or lytic bone metastases, responds only transiently to chemotherapy, and most survive less than one year (PALMGREN et al., Semin Oncol., 34:22-9 (2007)). t-NEPC is becoming an important entity to recognize as all patients eventually develop resistance.

SUMMARY OF THE DISCLOSURE

In accordance with this invention, AURKA and MYCN represent new prognostic molecular markers, and their overexpression or amplification in primary PCa identify patients predisposed to the development of lethal NEPC, who will benefit from early intervention.

In one aspect, this invention provides a method of subtyping prostate cancer based on determining the presence of overexpression or amplification of the AURKA gene and/or the MYCN gene.

In another aspect, this invention is directed to kits suitable for use in practicing the method of subtyping, which may include one or more nucleic acid reagents, one or more antibody reagents, or a combination thereof.

In a further aspect, this invention is directed to therapeutic methods of treating prostate cancer based on a prescreening or preselection step to identify those prostate cancer subjects who are positive for overexpression and/or amplification of at least one of AURKA and MYCN, and administering an AURKA and MYCN antagonist to an identified subject.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIG. 2. Evaluation of Aurora Kinase and N-Myc: (A) Gene expression of AURKA in Benign Prostate Tissue, PCA, and NEPC, as measured by RNA-Seq. RPKM=Reads per kilobase of exon per million mapped reads. (B) Gene expression of AURKA in Benign Prostate Tissue, PCA, and NEPC, as measured by RNA-Seq. RPKM=Reads per kilobase of exon per million mapped reads (C) Table summarizing IHC and FISH data from tumors from large cohort of PCA, NEPC, and benign prostate (D) Representative example of positive Aurora kinase A overexpression by IHC in MEPC. (E) MYCN and AURKA amplification by FISH in human NEPC. Green=Centromeric Control Probes, Red=AURKA and MYCN loci as labeled in NEPC. (F) mRNA expression of AURKA in Benign Prostate Tissue, PCA, and NEPC, as measured by RNA-Seq, annotated below for cases harboring AURKA gene amplification. (G) The levels of AURKA, B and C mRNAs as measured by real-time quantified RT-PCR of 6 out of the 7 NEPC tissue samples (1 NEPC sample had mixed NEPC/PCA phenotype and so was not included) relative to 7 PCA samples.

DETAILED DESCRIPTION

Figure 1A:
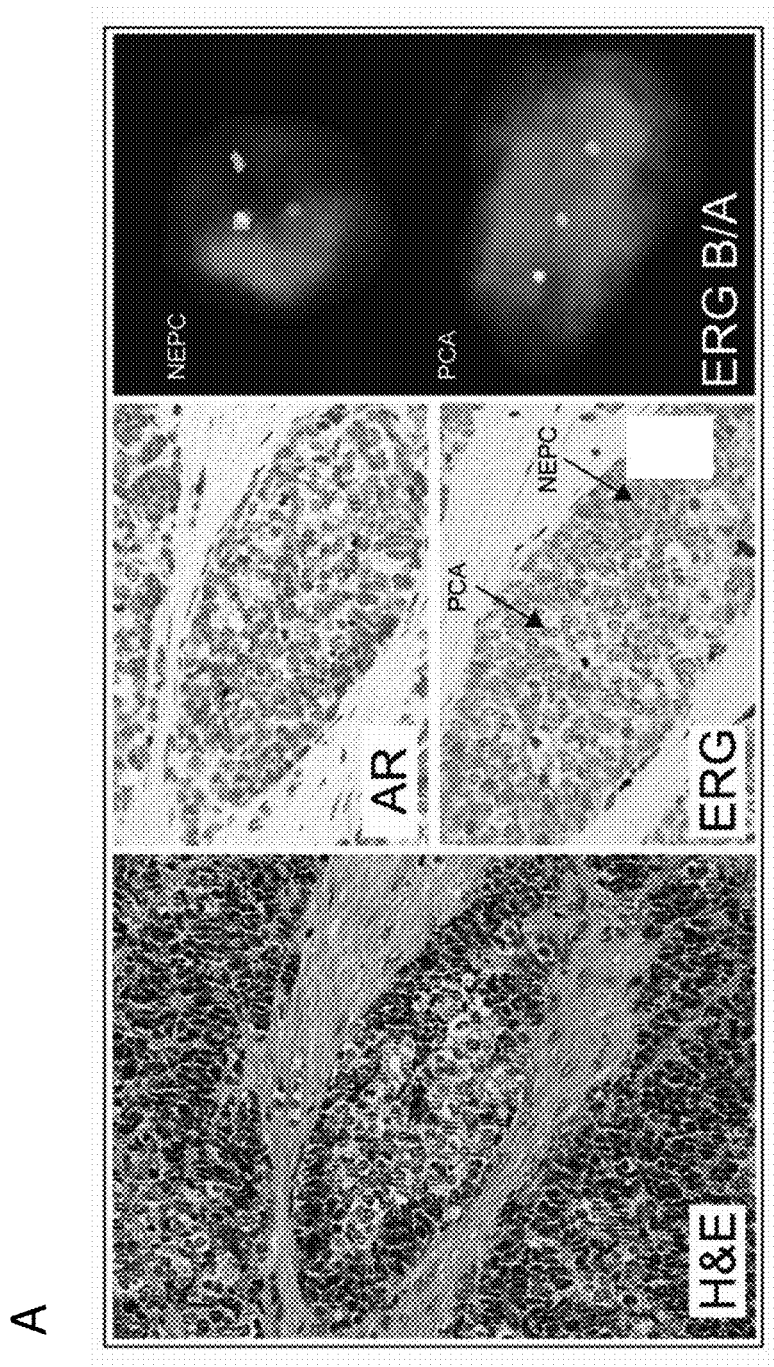
FIG. 1. Characterization of NEPC: (A) Tumor with mixed features of NEPC and PCA. Hematoxylin and eosin (H&E) staining, immunohistochemical analysis for androgen receptor (AR) and ERG, and FISH for ERG breakapart (indicating gene fusion). (B) Gene Expression of select genes comparing NEPC and PCA, including neuroendocrine associated genes (SYP, CHGB, CHGA), EZH2, MIB1 (Ki67), PSMA, AR, and androgen regulated genes (NKX3-1, KLK3 (PSA), TMPRSS2). (C) Graphical representation of the genomic landscape of PCA (in order of increasing Gleason Score) and NEPC, as determined by Affymetrix 6.0 oligonucleotide array (Red=Copy Number Gain, Blue=Copy Number Loss, White=No Change).

In an initial study, the inventors discovered significant overexpression and gene amplification of AURKA and MYCN in 40% neuroendocrine prostate cancer (NEPC) and a small percentage (5%) of prostate adenocarcinoma (PCa). The inventors subsequently investigated primary PCa from patients who later developed NEPC, and detected AURKA amplification in overall 64% primary PCa with concurrent MYCN amplification in a significant proportion of cases. Consistent with these findings on a molecular level, the histological features of prostate tumors (both primary and metastatic) from these patients were found to be heterogeneous, encompassing both pure neuroendocrine small cell carcinoma and mixed tumors with areas of poorly differentiated adenocarcinoma. Further, the inventors have shown that AURKA and MYCN functionally cooperate to induce a neuroendocrine phenotype in prostate cells, and that there was significant enhanced sensitivity of NEPC (and MYCN overexpressing PCa) to Aurora kinase inhibitor therapy both in vitro and in vivo, with complete suppression of neuroendocrine marker expression following treatment. Therefore, in accordance with this invention, AURKA and MYCN amplification or overexpression represent new prognostic molecular markers, and their presence in primary PCa identify patients predisposed to the development of lethal NEPC, who will benefit from early intervention with an antagonist of AURKA or MYCN or the encoded proteins. The various aspects and embodiments of this invention are further described hereinbelow.

Methods of Subtyping Prostate Cancer

In one aspect, this invention provides a method of subtyping prostate cancer based on determining the presence of overexpression or amplification of the AURKA gene and/or the MYCN gene.

The term "subtyping", as used herein, means classifying a prostate cancer subject into a distinct subgroup based on whether there is overexpression or amplification of at least one of AURKA or MYCN in a prostate cancer sample from the subject. For example, considering a subject who has been diagnosed by traditional means to have prostate cancer, but has not received any hormone therapy (i.e., hormone naïve), if determined to have overexpression or amplification of at least one of AURKA or MYCN in a prostate cancer sample, such subject is considered herein to fall within a subgroup that is predisposed (i.e., at substantially higher risk than a patient without the overexpression or amplification) to developing lethal NEPC, and will likely respond to an AURKA or MYCN antagonist as further defined herein. In another example, considering a subject who has been diagnosed to have prostate cancer and has been taking hormone therapy, if the subject, prior to manifesting phenotypes of NEPC, is determined to have overexpression or amplification of at least one of AURKA or MYCN in a prostate cancer sample, such subject is also considered to fall within a subgroup that is predisposed to progressing into NEPC and will likely respond to an AURKA or MYCN antagonist. In still another example, for a prostate cancer subject who has begun to manifest phenotypes of NEPC, if the subject is determined to have overexpression or amplification of at least one of AURKA or MYCN in a prostate cancer sample, such subject is considered to fall within a subgroup that will likely respond to an AURKA or MYCN antagonist.

The term "phenotypes of NEPC", as used herein, refers to the aggressive characteristics of this type of prostate cancer, including its frequent metastasis to visceral organs, only transient response to chemotherapy, and short survival after diagnosis. Histologically, NEPC is characterized by the presence of small, round, blue neuroendocrine carcinoma cells, which do not express androgen receptor or secrete prostate specific antigen (PSA), but usually express neuroendocrine markers such as chromogranin A, synaptophysin, and neuron-specific enolase.

In contrast with traditional means of diagnosing or identifying NEPC, the present invention provides AURKA and MYCN as new prognostic molecular markers for defining a subgroup of prostate cancer that has distinct disease progression and response to therapy, irrespective of the stage of prostate cancer.

The present method is applicable to any mammalian subject, particularly human subject, and is premised on determining the presence of overexpression or amplification of the AURKA gene or the MYCN gene.

To evaluate the expression or amplification of AURKA or MYCN, a biological sample is taken from a subject under examination. Sample sources suitable for use include any biological specimen that may contain prostate cancer cells, such as tissue, urine, blood, semen, prostatic secretions or prostate cells. Methods of procuring cell and tissue samples are well known to those skilled in the art, including, for example, tissue sections, needle biopsy, surgical biopsy, and the like. For a cancer patient, cells and tissue can be obtained from a tumor. A cell or tissue sample can be processed to extract, purify or partially purify, or enrich or amplify the nucleic acids in the sample for further analysis. In a specific embodiment, a urine sample is collected immediately following a digital rectal examination (DRE), which often causes prostate cells from the prostate gland to shed into the urinary tract. Samples obtained from the above-identified sources can be further processed, for example, to enrich for prostate cancer cells or extract the nucleic acid or protein molecules from the cells. The processing may include obtaining the serum or plasma portion of blood, obtaining the supernatant or cell pellet portion of urine, homogenization of tissue, lysis of cells, and the like.

The AURKA gene encodes Aurora kinase A, one of three Aurora serine and threonine kinases that function as key regulators of the mitosis process. The nucleic acid sequence of the human AURKA gene and its encoded amino acid sequence are readily available in the art (GenBank Accession No. NM_003600). While AURKA has been previously reported to be overexpressed in a number of cancers including primary prostate cancer (Lee et al., *Cancer Res.* 66 (10): 4996-5002 (2006), the overexpression reported is relative to a normal, healthy control population. As disclosed herein, however, the overexpression of AURKA is relative to the average expression level in subjects having primary prostate cancer and identifies a distinct subgroup of prostate cancer. Amplification of AURKA has also been reported herein for the first time by the inventors.

The MYCN gene encodes N-Myc, a proto-oncogenic transcription factor which plays a role in cell proliferation and apoptosis. The nucleic acid sequence of the human MYCN gene and its encoded amino acid sequence are readily available in the art (GenBank Accession No. NM_005378). MYCN has been reported to be overexpressed and amplified in neuroblastoma (see, e.g., Lutz, *Cancer Letters* 180: 107-119 (2002)). However, overexpression and amplification of MYCN have been identified herein for the first time in prostate cancer, defining a distinct subgroup of prostate cancer.

In some embodiments, the subject method of subtyping prostate cancer is based on determining the presence of overexpression of at least one of AURKA or MYCN, i.e., either or both of AURKA or MYCN.

The term "overexpression" of a gene, as used herein, means that the gene is expressed, i.e., transcribed, at an elevated level, resulting in elevated levels of the mRNA and the encoded protein. By "elevated level" is meant the level is significantly increased as compared to control level, e.g., an increase by at least 50%, 75%, 100% (twice the control level), 2 fold, 3 fold, 4 fold, 5 fold, 6 fold, 7 fold, 8 fold, 9 fold, 10 fold, or greater. As described above, the control level is the average level of gene expression in overall prostate cancer population, and can be a pre-determined value or range of values.

The level of mRNA of a particular gene can be measured using well known techniques, including, RNA-Seq, PCR (e.g., RT-PCR, including quantitative PCR), and Northern Blot analysis, among others. The Examples section below specifically illustrates the practice of both RNA-Seq and RT-PCR techniques in assessing the mRNA levels of AURKA or MYCN.

Overexpression of AURKA and MYCN at the protein levels can be detected by using antibodies specific for Aurora kinase A and N-Myc, respectively, in various assays such immunoblot (Western blot), immunohistochemistry, immunofluorescence, immunoprecipitation, and ELISA, for example.

In other embodiments, the subject method of subtyping prostate cancer is based on determining the presence of amplification of at least one of AURKA or MYCN.

The term "amplification" of a gene, as used herein, refers to an increase in the copy number of the gene present in the genome of a cell. A normal diploid cell typically has two copies of each chromosome and the genes contained therein. Thus, amplification of a gene means the presence of at least 3 or 4 copies of the gene in a cell.

The copy number of a gene can be determined using a nucleic acid probe that specifically hybridizes to the gene. Nucleic acid probes for purposes of specific hybridization should be at least 15 nucleotides in length to permit specific hybridization to a target gene, and can be 50, 100, 200, 400, 600, 800, 1000 bp or more nucleotides in length, or of a length ranging between any of the two above-listed values. A nucleic acid probe designed to specifically hybridize to a target gene can also include the full length sequence or a fragment of the gene.

By "specifically hybridize" it is meant that a nucleic acid probe binds preferentially to a target gene under stringent conditions, and to a lesser extent or not at all to other genes. "Stringent conditions" in the context of nucleic acid hybridization are known in the art, e.g., as described in Sambrook, *Molecular Cloning: A Laboratory Manual* ($2^{nd}$ ed.) vol. 1-3, Cold Spring Harbor Laboratory, Cold Spring Harbor Press, New York (1989). Generally, highly stringent hybridization and wash conditions are selected to be about 5° C. lower than the thermal melting point for a specific sequence at a defined ionic strength and pH. An example of highly stringent hybridization conditions is 42° C. in standard hybridization solutions. An example of highly stringent wash conditions include 0.2×SSC at 65° C. for 15 minutes. An example of medium stringent wash conditions is 1×SSC at 45° C. for 15 minutes. An example of a low stringency wash is 4×-6×SSC at room temperature to 40° C. for 15 minutes.

The hybridized nucleic acids can be detected by detecting one or more labels attached to the probe nucleic acids. The labels can be incorporated by a variety of methods known in the art, and include detectable labels such as a fluorescent compound, radio isotope, enzymes, colloidal gold particles, among others. Alternatively, the probes can be conjugated with one member of a binding pair, and the other member of the binding pair is conjugated with a detectable label. Binding pairs suitable for use herein include biotin and avidin, and hapten and a hapten-specific antibody.

In a specific embodiment, fluorescence in-situ hybridization (FISH) is used to assess the copy number of AURKA or MYCN. In a FISH assay, a gene-specific nucleic acid probe is labeled with a fluorescent compound, and the presence of amplification is determined based on observation of 3 or 4 gene-specific (i.e. AURKA or MYCN) signals on average per nuclei compared to two reference signals per nuclei.

In another embodiment, a single nucleotide polymorphism (SNP) oligonucleotide array is used to assess the copy number change of AURKA or MYCN. Copy number alterations (genomic gain or loss) of a genomic locus of interest (e.g., the AURKA or MYCN locus) can be detected in an SNP array using probes designed based on SNP(s) of the target genomic locus.

In other embodiments, the method of subtyping prostate cancer involves evaluation of both the expression level and gene copy number of at least one of AURKA or MYCN, and the prognosis is determined based on the presence of both overexpression and amplification of one or both genes.

In some embodiments, analysis of AURKA or MYCN is combined with examination of whether an ERG gene rearrangement has occurred. As disclosed herein, 100% concordance has been observed between ERG gene rearrangement and primary PCa that later developed into metastatic t-NEPC. Thus, the presence of an ERG gene rearrangement provides confirmation for subtyping made based on the presence of overexpression and/or amplification of AURKA or MYCN. ERG gene rearrangement can be determined by a break-apart FISH assay or PCR analysis, as described in, e.g., Tomlins et al., (*Science* 310 (5748): 644-648 (2005), Perner et al. (*Cancer Res.* 66 (17): 8337-8341 (2006), and U.S. Published Application 2007/0212702. For example, a break-apart system can include two BAC clone probes spanning the neighboring centromeric region and telomeric region of the ERG locus, respectively. The two probes are separately labeled to eventually produce two signals of different colors, e.g., red and green signals. A nucleus without ERG rearrangement exhibits two pairs of juxtaposed red and green signals, i.e., two yellow signals. A nucleus with an ERG rearrangement will show break apart of one juxtaposed red-green signal pair resulting in a single red signal and a green signal for the rearranged allele, and a combined yellow signal for the non-rearranged allele.

Reagent Compositions And Kits

In a further aspect, this invention is directed to reagents and kits suitable for use in practicing the method of subtyping as described above.

In one embodiment, the invention provides a kit containing nucleic acid reagents for detecting the expression or copy numbers of AURKA or MYCN. In a specific embodiment, the kit includes a nucleic acid reagent that detects the expression or copy number of AURKA, and a nucleic acid reagent that detects the expression or copy number of MYCN. Additional nucleic acid reagents can be included in the kit, e.g., nucleic acids that specifically detect the mRNA of a control gene, or nucleic acids detect a control genomic region.

Nucleic acid reagents can include primers or primer pairs suitable for use in amplification (e.g., PCR, RT-PCR), probes suitable for use in a hybridization-based assay (e.g., Northern Blot, Southern Blot, or FISH). Nucleic acid primers designed for use in an amplification reaction can be as short as about 15 nucleotides, to 18-25 nucleotides or longer. Nucleic acid probes for use in a hybridization assay can be as short as 15 nucleotides to the full length of a gene of several kilo nucleotides or a substantial fragment thereof. Depending on the format of an assay used, the primers or probes can include an agent or compound that ultimately generates a detectable signal, or immobilized on a solid support.

In another embodiment, the invention provides a kit containing antibody reagents that detect Aurora kinase A and N-Myc proteins, respectively. Antibodies to Aurora kinase A and antibodies to N-Myc can be prepared by using routine techniques, and can conjugate to an agent or compound that allows for generation of a detectable signal.

In other embodiments, the kit can include a combination of one or more nucleic acid reagents and one or more antibody reagents.

Methods Of Treatment

Currently there is no standard treatment for patients with NEPC, accounted for in part by its poor molecular characterization. This disclosure has demonstrated that Aurora kinase A and N-Myc interact with each other to induce NEPC, and has further demonstrated the dramatic and preferential sensitivity of NEPC preclinical models to Aurora kinase inhibition. Accordingly, a further aspect of the invention is directed to therapeutic methods of treating prostate cancer.

The therapeutic approach disclosed herein is premised on a prescreening or preselection step to identify those prostate cancer subjects that are positive for overexpression and/or amplification of at least one of AURKA and MYCN. This prescreening can be applied to a population of prostate cancer subjects, or to a particular prostate cancer subject who has been recently diagnosed but has not taken hormone therapy, or to a particular prostate cancer subject is undergoing hormone therapy. Once a subject has been positively identified, the subject is treatment with administration of an antagonist of AURKA or MYCN.

The term "antagonist", as used herein, refers to a molecule that inhibits the expression level of a relevant gene (AURKA or MYCN), or alternatively, inhibits the activity or function of the encoded protein of the relevant gene. For example, an antagonist of AURKA includes a nucleic acid molecule which reduces the level or activity of AURKA mRNA, such as an siRNA or antisense molecule; an antibody against Aurora kinase A that inhibits or reduces the activity of Aurora kinase A; and a small molecule compound that inhibits or reduces the activity of Aurora kinase A. Similarly, an antagonist of MYCN includes a nucleic acid molecule which reduces the level or activity of MYCN mRNA, such as an siRNA or antisense molecule; an antibody against N-Myc that inhibits or reduces the activity of N-Myc; and a small molecule compound that inhibits or reduces the activity of N-Myc.

Nucleic acid-based antagonists, such as siRNAs and antisense molecules, can be designed given the sequence of a target gene, and made either synthetically or in cells from an exogenously introduced vector (e.g., a plasmid) to achieve suppression of expression of a gene of interest.

Small molecules refer to organic compounds, organometallic compounds, salts of organic and organometallic compounds, saccharides, amino acids, and nucleotides, which typically have molecular weights of less than approximately 1200 or 1000 Daltons, in some embodiments less than 800 Daltons. Small molecule inhibitors of Aurora kinase A have been documented in the art, including VX-680/MK-0457, PHA-739358, MLN8054, MLN8237, SNS-314CYC116, PF-3814735, ENMD2076, AT-9283, R-763/AS-703569, as described by Cheung et al. (*Expert Opin. Investig. Drugs* 18(4): 379-398, 2009, incorporated herein in its entirety), and AMG900 (a small molecule inhibitor of Aurora kinase A, B, and C).

TABLE 1
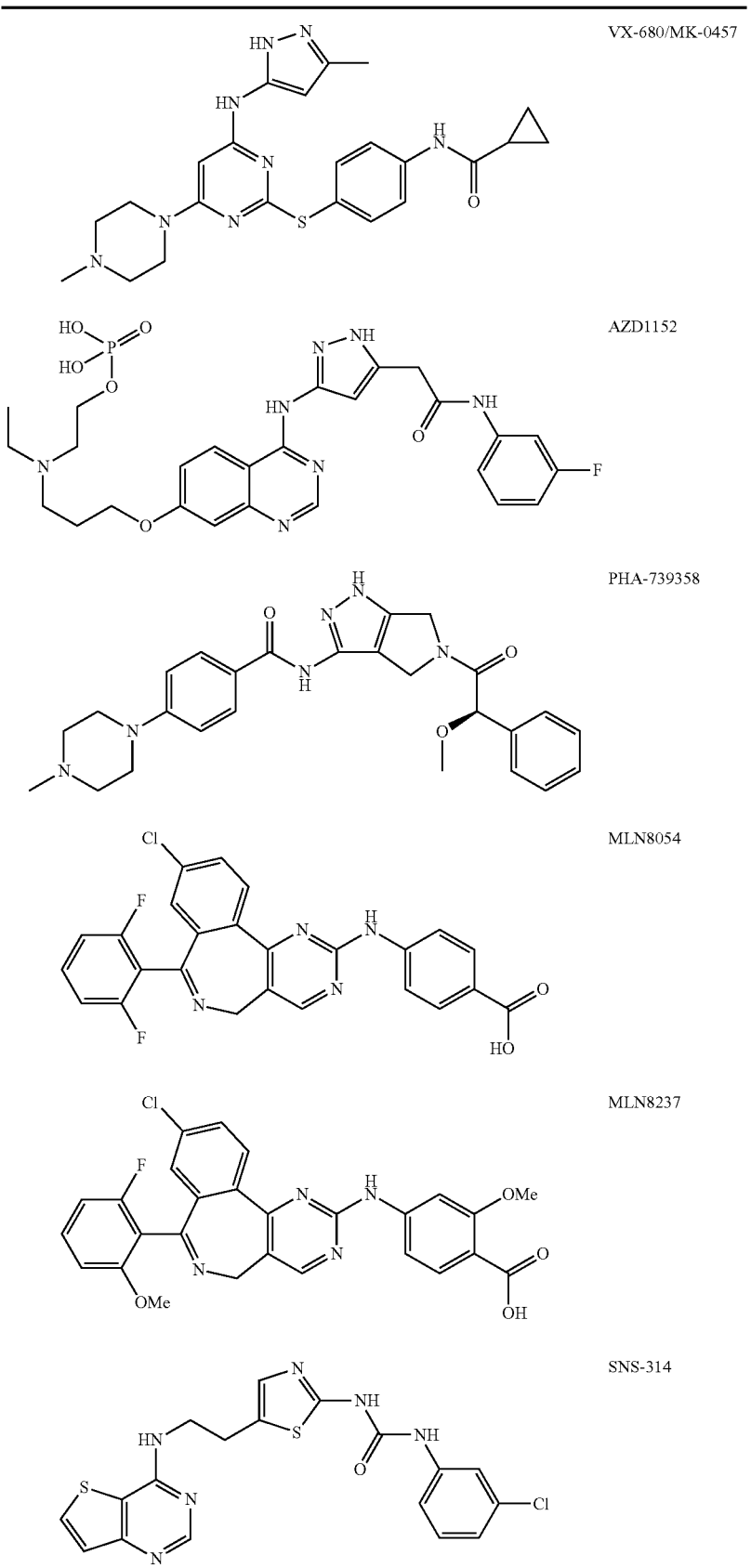

TABLE 1-continued
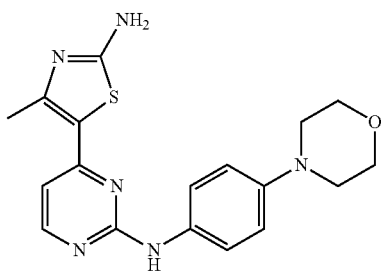 [SMILES: Cc1nc(N)sc1-c1ccnc(Nc2ccc(N3CCOCC3)cc2)n1] CYC116
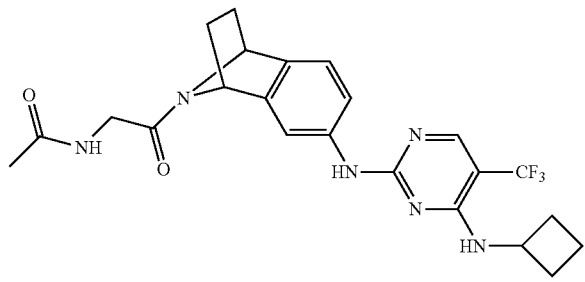 [SMILES: CC(=O)NCC(=O)N1C2CCC1c1cc(Nc3ncc(C(F)(F)F)c(NC4CCC4)n3)ccc12] PF-3814735
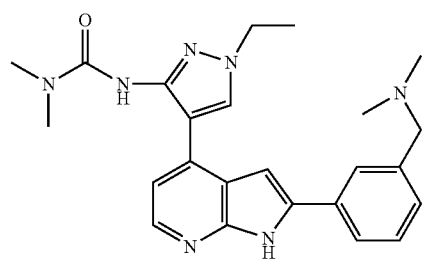 GSK1070916
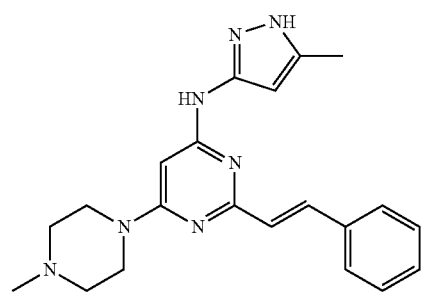 ENMD 2076 (ENMD-981693: free base)
L (+) Tartaric acid
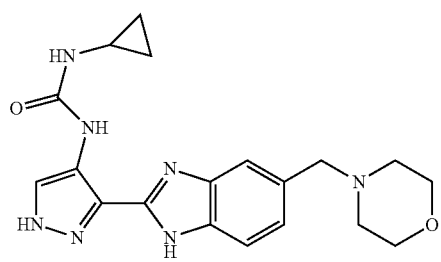 [SMILES: O=C(Nc1c[nH]nc1-c1nc2cc(CN3CCOCC3)ccc2[nH]1)NC1CC1] AT-9283

TABLE 1-continued

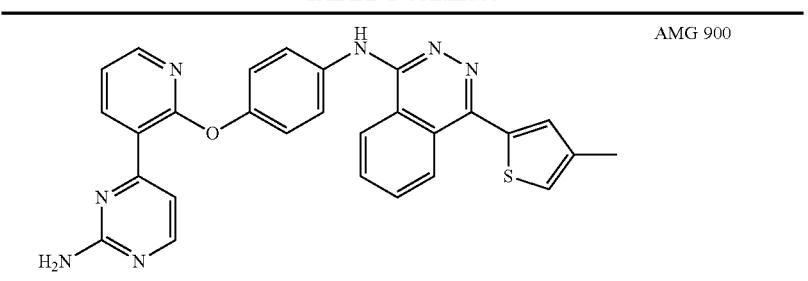

AMG 900

Whether an antagonist is effectively inhibiting the expression of AURKA or MYCN or inhibiting the activity of the encoded protein can be assessed by determining whether the administration of the antagonist has reduced gene expression of AURKA or MYCN in samples taken from the subject under examination, or has prevented, reduced, or eliminated expression of one or more neurocrine markers in samples taken from the subject.

An AURKA or MYCN antagonist can be administered in combination with other cytotoxic chemotherapeutic compound(s) suitable for treating prostate cancers.

Active compounds (i.e., an AURKA or MYCN antagonist, and/or other chemotherapeutic compound(s)) can be combined with a pharmaceutically acceptable carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

As used herein, a pharmaceutically acceptable carrier includes any and all solvents, dispersion media, isotonic agents and the like. Except insofar as any conventional media, agent, diluent or carrier is detrimental to the recipient or to the effectiveness of the active ingredients contained therein, its use in practicing the methods disclosed herein is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

The concentration of an antagonist in formulations may range from as low as about 0.1% to as much as 15 or 20% by weight and can be selected based on the nature of a particular antagonist used, the mode of administration selected, among other considerations. A pharmaceutical formulation containing an antagonist can be given to a subject by standard routes, including ingestion, or injections via an intravenous, intraperitoneal, subcutaneous, transdermal, intramuscular, intranasal, or sublingual route. The amount of antagonist administered to be effective may depend on the condition of the patient (e.g., age, body weight, health and disease stage), and the nature of the antagonist. The precise amount of an antagonist to be effective can be determined by a skilled physician.

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

This Example describes experiments in which 7 NEPC, 30 PCA, and 5 benign prostate tissue (BEN) were profiled by using Next Generation RNA-sequencing and oligonucleotide arrays, and the findings were validated on tumors from a large cohort of patients (37 NEPC, 169 PCA, 22 BEN) using IHC and FISH. Significant overexpression and gene amplification of AURKA and MYCN were discovered in 40% of NEPC and 5% of PCA, respectively, and it is shown herein that that they cooperate to induce a neuroendocrine phenotype in prostate cells. There was dramatic and enhanced sensitivity of NEPC (and MYCN overexpressing PCA) to Aurora kinase inhibitor therapy both in vitro and in vivo, with complete suppression of neuroendocrine marker expression following treatment.

Results

The inventors evaluated forty-five NEPC tumors, and observed a spectrum ranging from pure small cell carcinoma to tumors with mixed features of both PCA and NEPC. The TMPRSS2-ERG gene fusion was detected by Fluorescence In Situ Hybridization (FISH) break-apart assay in 44% of NEPC. Importantly, in tumors demonstrating both PCA and NEPC foci, there was perfect concordance with regards to the TMPRSS2-ERG status (FIG. 1A). NEPC foci lacked ERG protein expression by immunohistochemistry (IHC), even in tumors harboring the TMPRSS2-ERG rearrangement, with a sharp margin separating NEPC and PCA components in mixed tumors. This margin also corresponded directly to presence or absence of androgen receptor (AR) expression (in PCA and NEPC, respectively), consistent with ERG protein expression being driven by androgen and requiring AR signaling.

Using Next Generation RNA sequencing (RNA-Seq) and oligonucleotide arrays, the inventors sequenced seven NEPC and thirty localized PCA tumors.

Figure 1B:
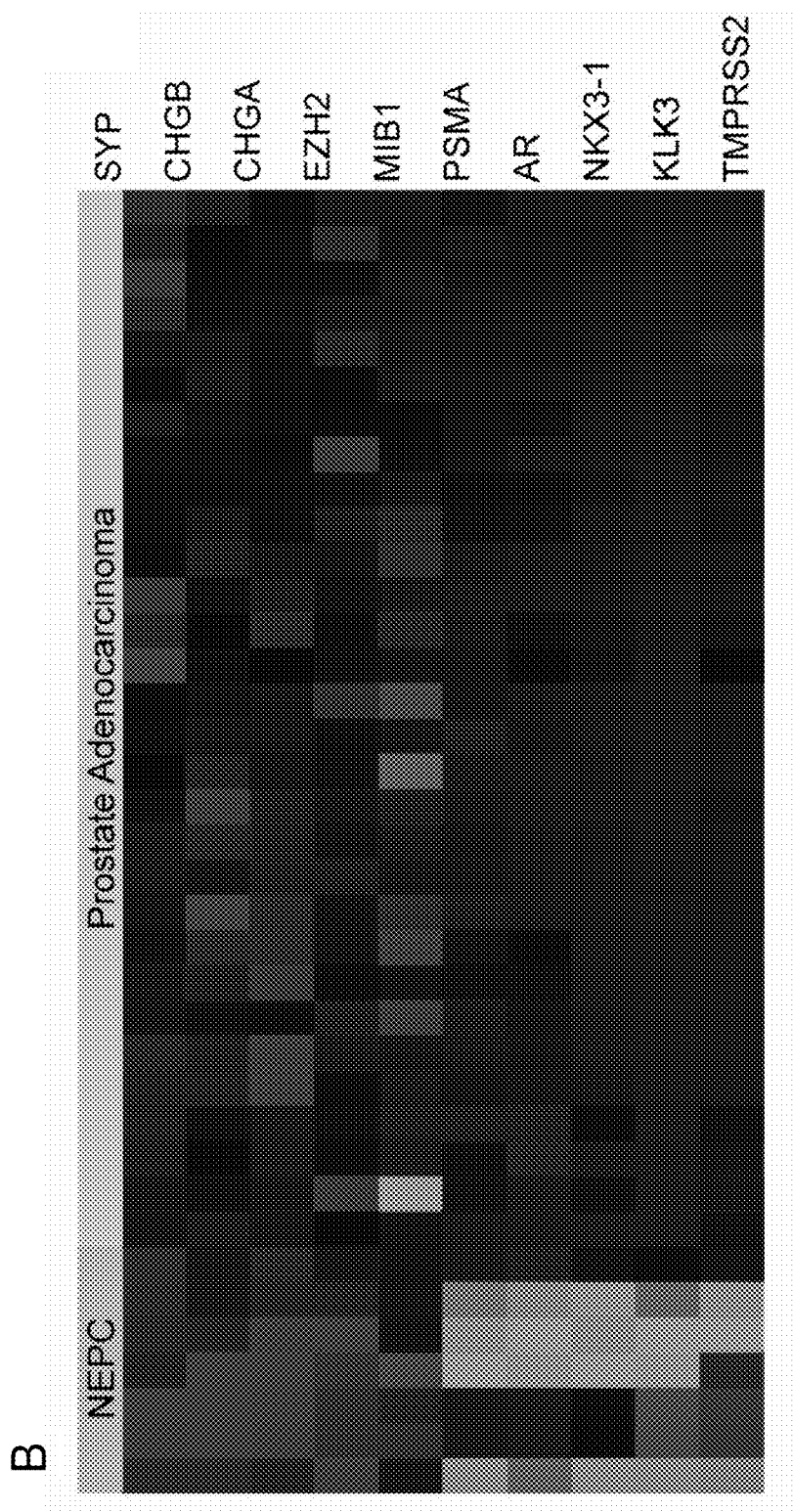
Figure 1C:
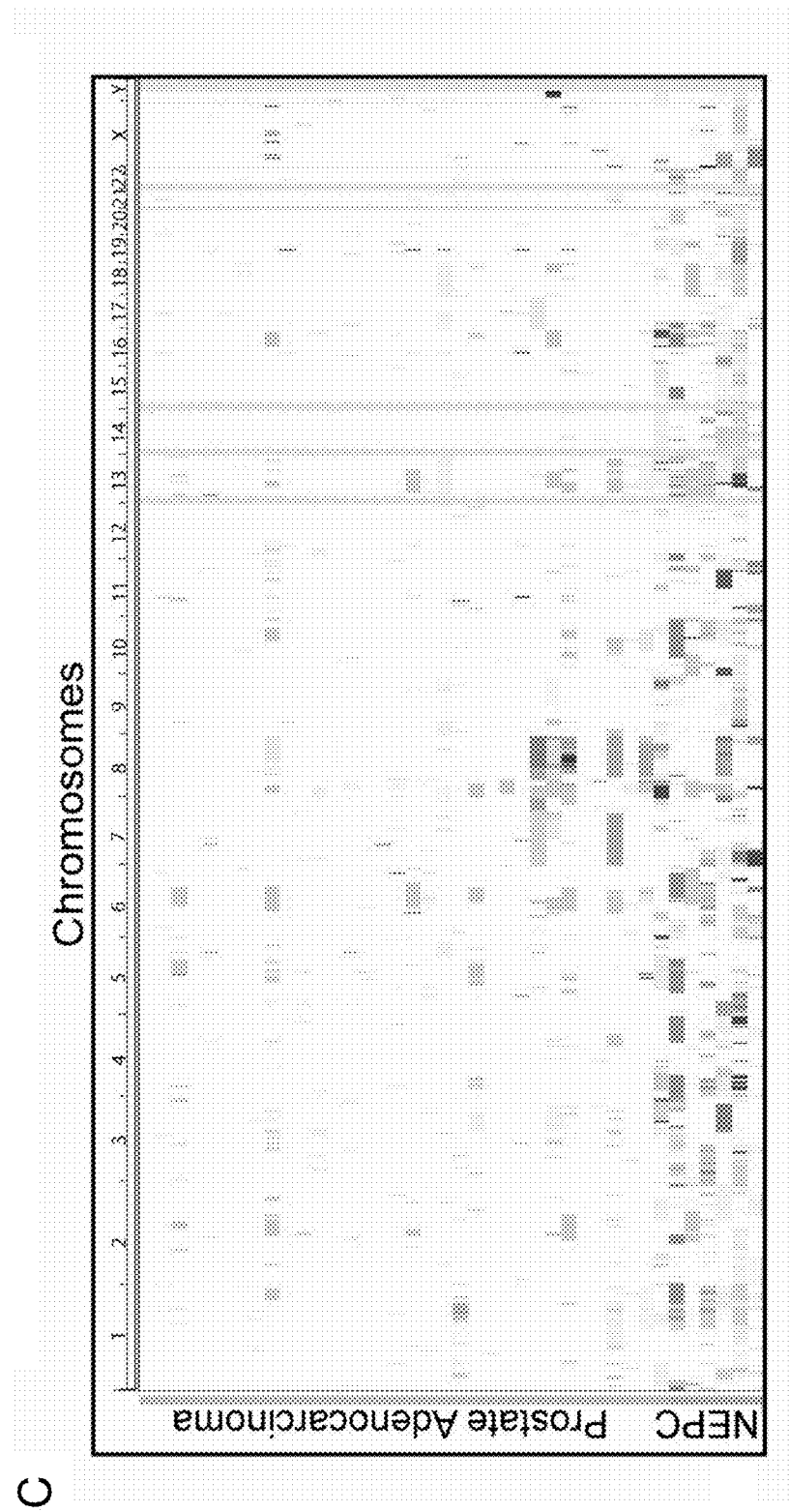

There were significant gene expression differences between NEPC and PCA, with 936 of 25,932 evaluated genes showing differential expression after correction for multiple hypothesis (Benjamini-Hochberg P<0.001). There were no global gene expression differences between primary and secondary NEPC. As expected, NEPC demonstrated low expression of known androgen-regulated genes (e.g., KLK3 (PSA), TMPRSS2, NXK3.1) and high expression of neuroendocrine-associated genes (e.g., CGA and SYP), though there were some tumors with mixed molecular features (FIG. 1B). EZH2, a polycomb gene shown to be associated with aggressive behavior in a number of cancer types including prostate (VARAMBALLY et al., Nature, 419: 624-9 (2002)), was significantly overexpressed in NEPC compared to PCA (P=0.0001). Somatic copy number alteration assessment revealed discrete, statistically significant differences in the number of genomic amplifications and deletions in NEPC as compared to PCA (FIG. 1C).

After integration of gene expression and copy number data, the inventors evaluated for targetable lesions and discovered significant overexpression and gene amplification of AURKA (Aurora kinase A) in NEPC compared to PCA ($P=1.46\times10^{-5}$) (FIG. 2A,2F). AURKA mRNA was overexpressed in all 7 cases, but amplified in 4/7 NEPC. AURKA amplification was associated with overexpression ($P=0.0006$), but AURKA overexpression also occurred without amplification (potentially through other mechanisms). Within NEPC, the level of AURKA overexpression was not differential based on amplification (FIG. 2F). AURKA is a serine/threonine kinase involved in mitotic spindle formation, centrosome separation, and G2-M transition during the cell cycle (ZHOU et al., *Nat Genet.*, 20:189-93 (1998)), although it also has oncogenic properties (ZHOU et al., *Nat Genet.*, 20:189-93 (1998)).

Next, the inventors queried the dataset for MYCN gene expression and discovered significant overexpression in NEPC compared to PCA ($P=0.0005$) (FIG. 2B). N-myc is a transcription factor in the MYC family, involved in nervous system development and not normally expressed in the prostate (STRIEDER et al., *Cancer Lett.*, 180:107-19 (2002)) or previously linked to prostate cancer. The Affymetrix 6.0 array did not have adequate coverage of the MYCN locus on 2p24 with the nearest markers 2.5 Kb from the 3' and 5' end of the gene, and was therefore suboptimal in evaluating for MYCN copy number gain.

The inventors screened benign prostate and prostate tumors from a larger cohort of patients (22 benign, 169 primary PCA, 37 NEPC) (FIG. 2C), and found AURKA was overexpressed by immunohistochemistry (IHC) in none of the benign prostate cases, 12% of PCA, and 76% of NEPC. AURKB was also over-expressed in NEPC although to a lesser degree, and AURKC was minimally expressed in either NEPC or PCA (FIG. 2G). In NEPC, there was strong cytoplasmic expression of Aurora kinase A in the majority of tumor cells (>50%), but in PCA represented <5% of tumor cells and expression was weaker and demonstrated a speckled pattern (FIG. 2D). AURKA was amplified by FISH in none of the benign prostate, 5% of PCA, and 40% of NEPC. Neither AURKB or AURKC were amplified. MYCN was amplified by FISH in none of the benign prostate, 4% of PCA, and 40% of NEPC. In nearly all positive cases (>90%), amplification of AURKA or MYCN was concurrent (Table 2).

TABLE 2

FISH data for AURKA and MYCN copy number gain in 22 Benign Prostate Tissue, 169 PCA, and 37 NEPC, showing concordance of AURKA and MYCN amplification in >90% of cases.

|  | AURKA+ | AURKA− | Total |
|---|---|---|---|
| MYCN+ | 20 | 1 | 21 |
| MYCN− | 2 | 183 | 185 |
| Total | 22 | 184 | 206 |

Notably, one patient who progressed from PCA to NEPC after three years demonstrated amplification of AURKA and MYCN in his primary PCA, suggesting that these genomic aberrations can arise early.

Figure 3C:
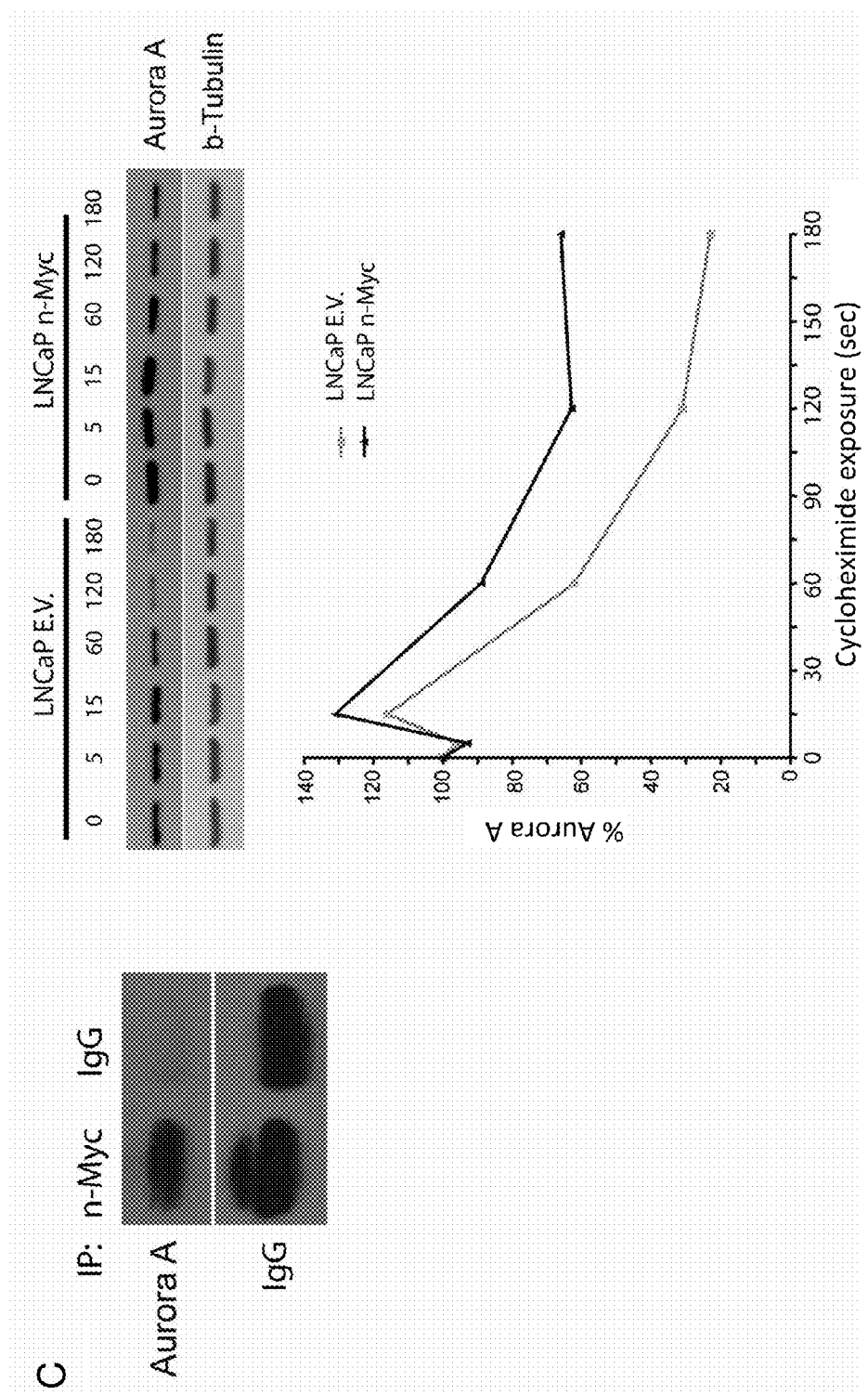
FIG. 3. (A) Immunoblot analysis for protein expression of Aurora kinase A, Phosphorylated histone 3 (P04-H3), neuron specific enolase (NSE) and synaptophysin (SYP) after transient transfection of MYCN, AURKA, or Empty Vector (EV) in RWPE-1 cells. BE(2)N is a neuroblastoma cell line as positive control for NSE. (B) Stable LNCaP cell line over-expressing N-myc compared to empty vector (EV): Immunoblot analysis for protein expression of N-myc, Aurora kinase A, P04-H3, NSE, SYP, PSA, AR, beta actin. qRT-PCR and microarray (MA) data showing induction of NSE (qRT-PCR) and EZH2 (MA) gene expression and suppression of AR (qRT-PCR) and androgen regulated genes (NKX3-1, TMPRSS2 (MA)). (C) Left: Immunoprecipitation of LNCaP-n-Myc cell lysates using antibodies directed against N-Myc or control IgG antibodies and Western blot using antibodies directed against Aurora kinase A (Aurora A) or control IgG antibodies. Right: LNCaP control (LNCaP E.V.) and LNCaP-n-Myc cells were treated with cycloheximide (CHX) for the indicated time (in minutes) and Aurora kinase A or beta-tubulin levels were assessed by immunoblotting. The normalized percent of Aurora kinase A relative to beta-tubulin and to time point 0 for LNCaP E.V. (gray line) or LNCaP-n-Myc (black line). (D) N-Myc directly binds to the SYP, NSE, and AR promoters in LNCaP-n-Myc cells and not LNCaP-EV. Not-to-scale schematic representation of SYP, NSE, and AR promoters showing the E-box sites (grey and black circles) indicated for each. The transcription start site for each gene is indicated with an arrow. Below each schematic are bar graphs showing the amount of enriched DNA (relative to input chromatin preparation) for each E-box site in the indicated cell lines following ChIP using either anti-N-Myc (right) or anti-IgG (left) antibodies. IMR-32 is a MYCN amplified neuroblastoma cell line. In IMR-32 cells, N-myc binds promoters of SYP and NSE, but not AR. (E) Quantitative PCR after siRNA transfection of AURKA or control nonsilencing siRNA (Scr) in NCI-H660 cells. This confirmed effective knockdown of AURKA mRNA expression after siRNA transfection, and resultant decrease in the neuroendocrine marker, neuron-specific enolase (NSE), expression following siRNA AURKA transfection.

Transfection of MYCN in either benign prostate RWPE-1 or LNCaP (PCA cells) induced expression of AURKA and phosphorylated histone 3 (a downstream marker of Aurora kinase activity (HSU et al., *Cell*, 102:279-91 (2000))) (FIG. 3A, B). Chromatin immunoprecipation (ChIP) of LNCaP cells stably transfected with MYCN revealed that N-myc did not bind the promoter of AURKA but did bind to E-box binding elements associated with the N-myc-responsive promoter of telomerase reverse transcriptase (hTERT) as previously described (SLACK et al., *Proc Natl Acad Sci USA*, 102:731-6 (2005)). Instead, the inventors found that the N-myc protein physically interacted with Aurora kinase A (as seen by co-immunoprecipitation) and enhanced Aurora kinase A protein stability (FIG. 3C).

Figure 3D:
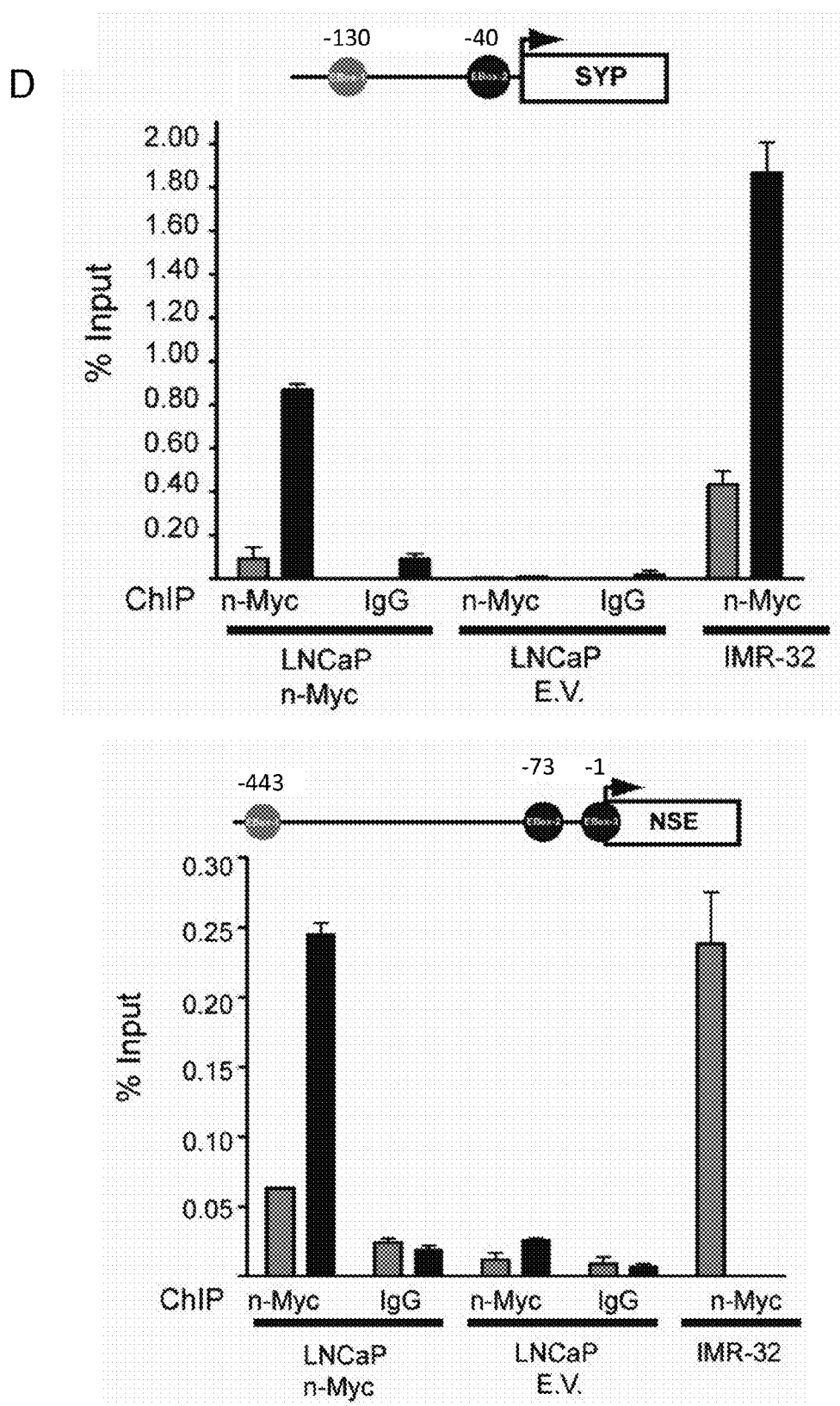
Figure 3D:
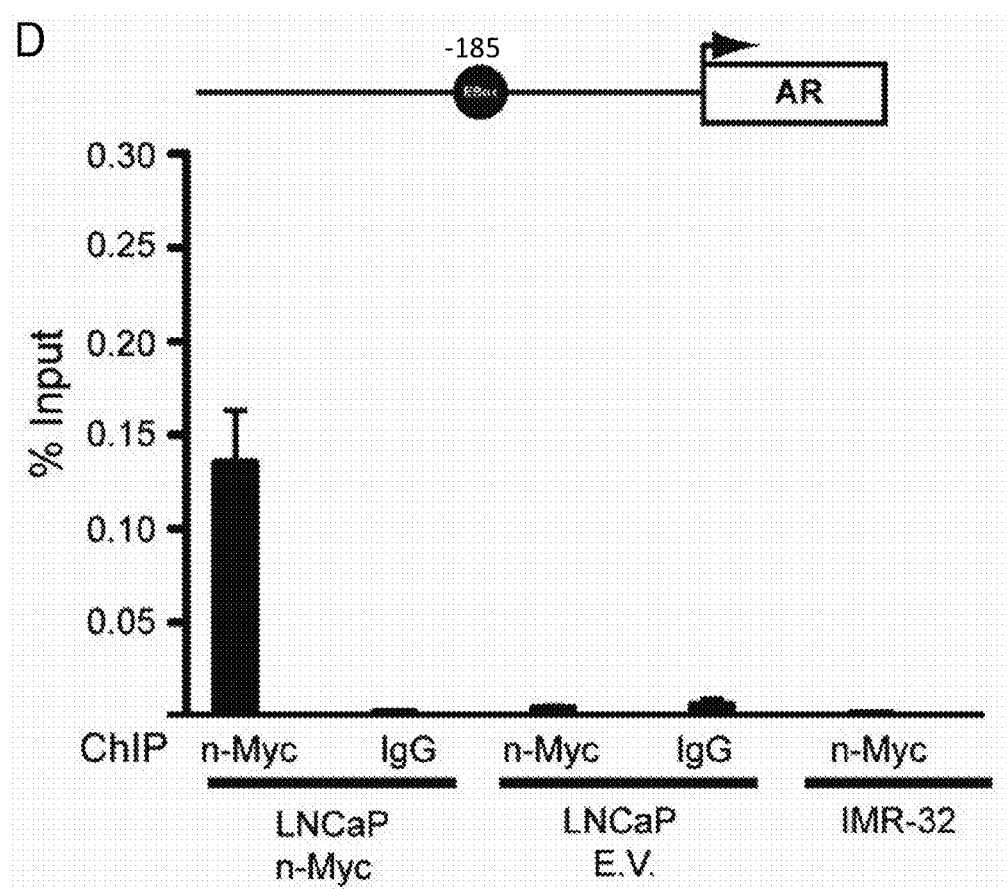
Figure 3E:
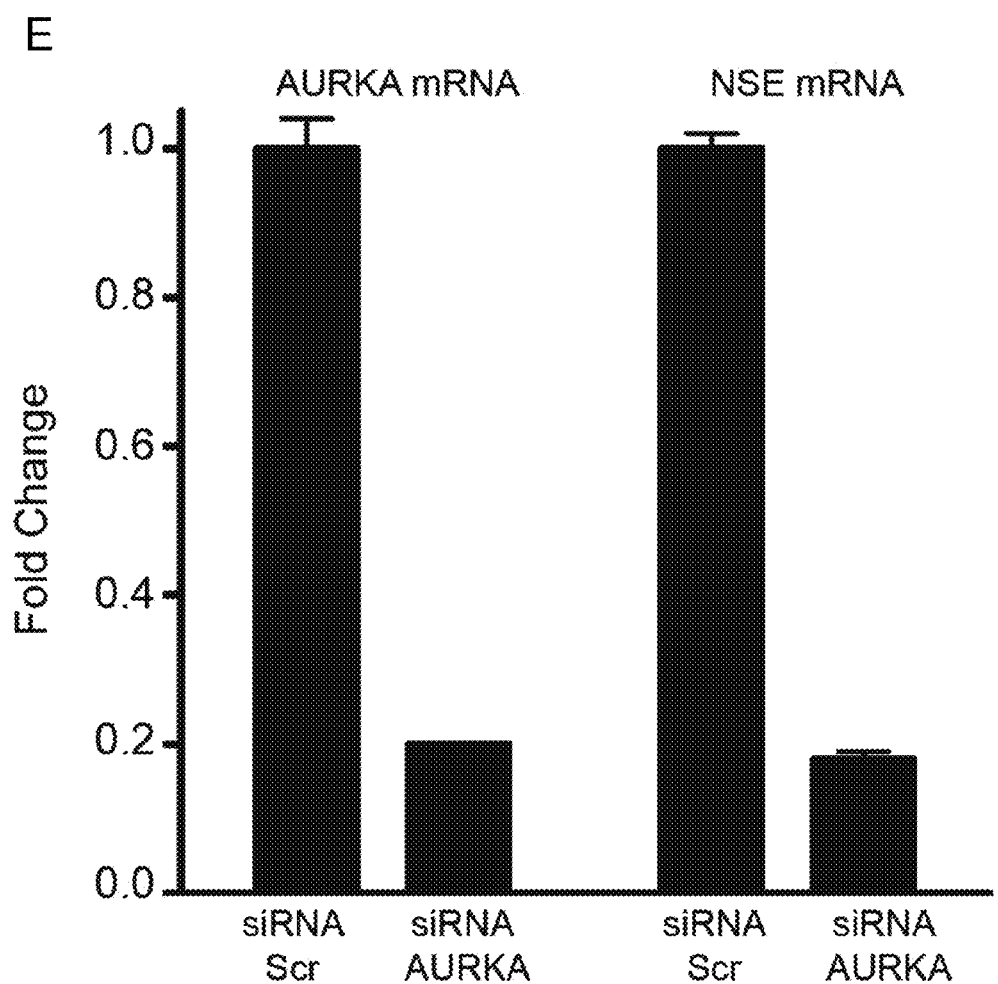

Overexpression of either AURKA or MYCN into RWPE-1 cells induced expression of the neuroendocrine markers, NSE and SYP, which are not normally expressed in benign prostate (FIG. 3A), suggesting that AURKA and MYCN may be involved in neuroendocrine differentiation. Knockdown of AURKA with siRNA suppressed NSE expression in the NEPC cell line, NCI-H660 (FIG. 3E). Furthermore, LNCaP cells stably transfected with MYCN (LNCaP-n-Myc) phenotypically resembled NEPC, with upregulation of the neuroendocrine marker NSE, downregulation of AR and androgen regulated genes (TMPRSS2, NKX3-1), and upregulation of EZH2 compared to control LNCaP cells (FIG. 3B). Chromatin immunoprecipitation revealed that N-myc binds the promoters of NSE, SYP, and AR, suggesting direct modulation of the neuroendocrine phenotype by transcription factor binding (FIG. 3D). In MYCN-amplified neuroblastoma cells (IMR-32), N-myc also bound NSE and SYP promoters, but not AR (suggesting N-myc binding of AR promoter may be prostate-specific).

Based on these findings, the inventors posited that treatment with an Aurora kinase inhibitor would have a preferential effect on NEPC compared to PCA. To test this hypothesis in vitro, the inventors used two experimental models: LNCaP cells stably transfected with MYCN (which phenotypically resemble NEPC), and the NCI-H660 cell line. NCI-H660 was originally derived at time of autopsy from a patient with small cell carcinoma initially thought to be lung cancer but later classified as prostate (CARNEY et al., *Cancer Res.*, 45:2913-23 (1985), VAN BOKHOVEN et al., *Prostate*, 57:205-25 (2003)). RNA sequencing revealed that NCI-H660 has a similar molecular signature as our NEPC tumors (including overexpression of AURKA and MYCN), and FISH also demonstrated AURKA and MYCN copy number gain as well as over-expression of phosphorylated Aurora A (compared to phosphorylated forms of Aurora B and C), as another measure of kinase activity status.

Figure 4C:
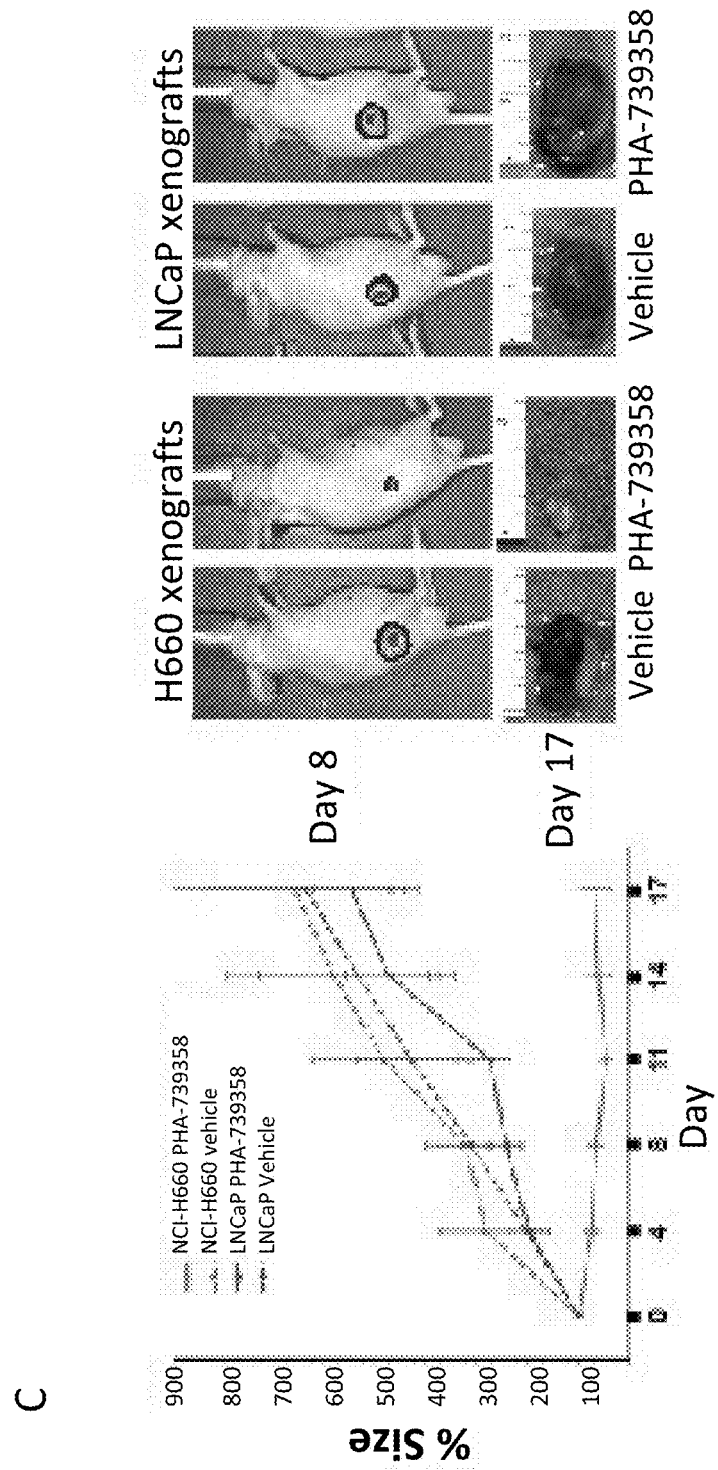
FIG. 4. NEPC demonstrates enhanced sensitivity to Aurora Kinase Inhibitor therapy compared to PCA (A) Viability assay of LNCaP cells transfected with MYCN or Empty Vector (EV) at 72 hours after treatment with vehicle or indicated doses of the pan-Aurora kinase inhibitor PHA-739358. (B) Viability assay of RWPE (blue circles), VCaP (gray diamonds), DU145 (gray triangles), and NCI-H660 (orange triangles) at 72 hours after treatment with vehicle or indicated doses of PHA-739358. (C) Percent tumor size after treatment of LNCaP (gray) and NCI-H660 (red) xenografts with vehicle (dotted lines) or PHA-739358 30 mg/kg IP BID (solid lines) twice a day for 5 days relative to day 0. Luciferase imaging at day 8 and tumor photographs at day 17 of representative tumors following treatment with either vehicle or PHA-73935. (D) Percent tumor size after treatment of LTL-362 xenografts with vehicle (dotted lines) or PHA-739358 30 mg/kg IP BID (solid lines) twice a day for 5 days relative to day 0. (E) Immunohistochemical staining for phosphorylated histone 3 (PO4-H3) in NCI-H660 or LNCaP tumors at day 4 of treatment with either vehicle or PHA-739358. (F) Immunohistochemistry for the neuroendocrine marker, synaptophysin, in NCI-H660 xenografts treated with vehicle (positive) and PHA-739358 (negative). Levels of AURKA mRNA in (G) and viability of (H) NCI-H660 cells following infection with different lentiviruses harboring short hairpins (sh) targeting either. GFP (control) or AURKA mRNA (for this 2 independent shAURKA were used). Viability was assessed at the indicated time points following infection. mRNA levels were assessed at day 2 following infection.
Figure 5:
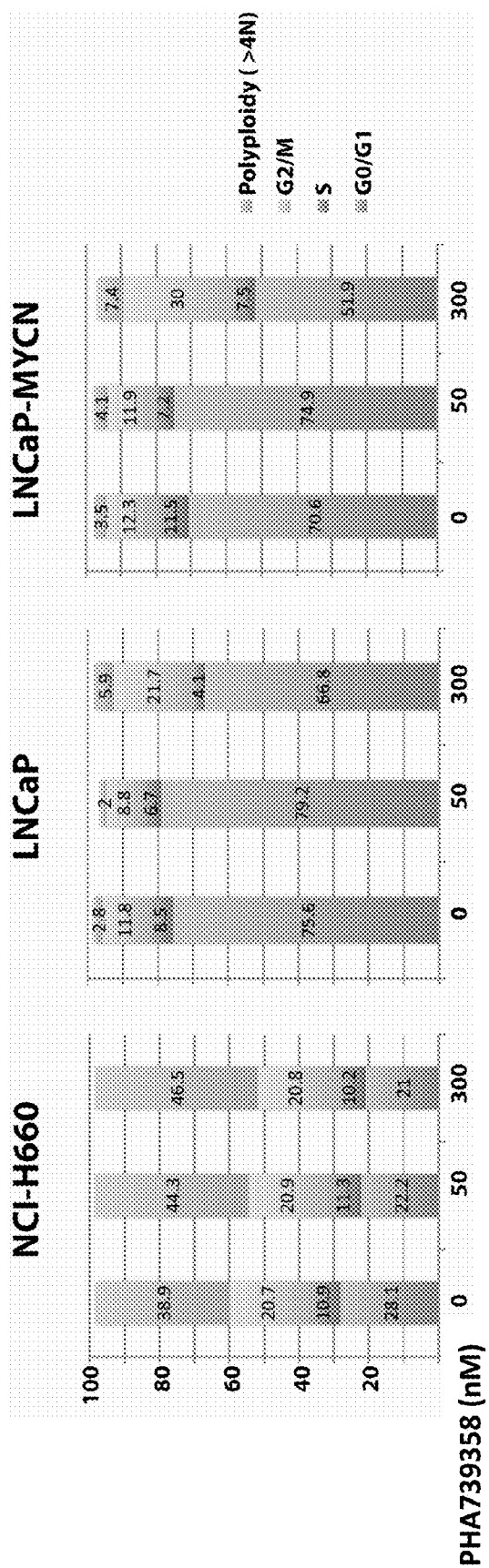
FIG. 5. FACs analysis of the indicated cells following 48 hours of PHA-739358 treatment.

LNCaP-n-Myc cells demonstrated enhanced in vitro sensitivity to the Aurora kinase inhibitor PHA-739358 (Nerviano Medical Sciences, Milan, Italy) compared to control LNCaP cells (LNCaP-EV) (FIG. 4A). Similarly, NCI-H660 also demonstrated enhanced sensitivity to PHA-739358 compared to two PCA cell lines (DU145, VCaP) and benign RWPE-1 cells (FIG. 4B). Knockdown of Aurora A in NCI-H660 with multiple shRNAs showed similar results (FIG. 4G-H). Given the role of Aurora kinase A in the cell cycle, the inventors performed FACS analysis of cells following PHA-739358 treatment confirming a dose dependent G2/M arrest with PHA-739358 treatment in LNCaP and LNCaP-MYCN cells. Polyploidy was induced by PHA-739358 in all cells (i.e., LNCaP, LNCaP-MYCN, and NCI-H660). However, there was no significant G2/M arrest in NCI-H660 cells, supporting our hypothesis that Aurora A may have alternative mechanisms of action in NEPC (FIG. 5).

Figure 4F:
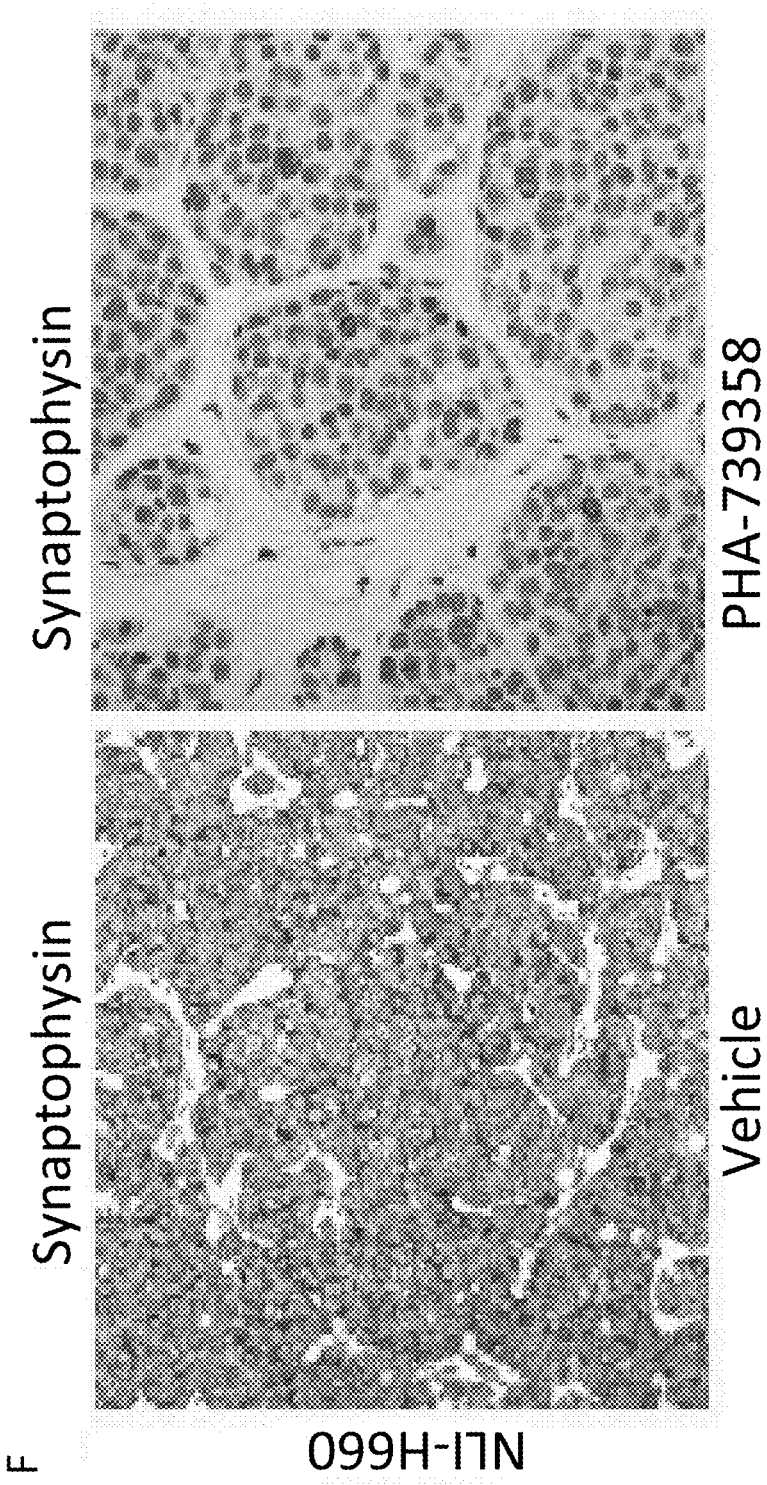

The inventors then tested PHA-739358 in xenografts using two NEPC models: 1) NCI-H660 xenografts, which appear histologically similar to NEPC, are positive for neuroendocrine markers by IHC, and though harboring the TMPRSS2-ERG gene fusion (SETLUR et al., *J Natl Cancer Inst.*, 100:815-25 (2008)), are negative for ERG protein (FIG. 4F), and 2) the LTL-352 xenograft, derived from patient with a history of metastatic PCA that progressed to NEPC after forty months of androgen deprivation therapy (TUNG et al., Prostate (2010)). When treated with PHA-739358, there was average tumor shrinkage of 50-87%, in both NCI-H660 and LTL-352 xenografts (P<0.001), compared to no effect in LNCaP xenografts (FIG. 4C, D) and a cytostatic effect in VCaP xenografts and was without significant toxicity as determined by body weight. Phosphorylated histone 3 expression was significantly inhibited in the treated NCI-H660 xenografts (indicating on-target drug effect) and not in the LNCaP xenografts (FIG. 4E). Notably, SYP expression was also completely suppressed in the treated NCI-H660 xenografts (FIG. 4F), again supporting a role of Aurora kinase in modulating the neuroendocrine phenotype.

Materials and Methods

Description of the Clinical Cohort. All tissue samples were collected as part of an Institutional Review Board (IRB) approved protocol at Weill Cornell Medical College (WCMC). De-identified frozen NEPCs were obtained from WCMC (tumor metastases obtained from lung, soft tissue, and spinal cord metastases), University of Michigan rapid autopsy program (metastases), Henri Mondor Hospital (prostatectomy case), University of Pittsburgh (biobank program), and University of British Columbia (metastatic tumor passaged as second generation xenograft). Additional formalin fixed-paraffin embedded (FFPE) NEPC tumors for validation studies were obtained from WCMC, University of Tubingen, and University of Pittsburgh. Frozen and FFPE localized PCA and benign prostate tissues were collected at time of radical prostatectomy at WCMC. All cases were reviewed by the study's pathologist (M.A.R.) and high density tumor foci with less than 10% stroma were selected for RNA and DNA extraction. Benign prostate samples were selected from blocks containing no tumor tissue, in order to minimize contamination.

RNA-Sequencing (RNA-Seq) and Copy Number Assessment. The complete transcriptomes of seven NEPC tumors, 30 prostate adenocarcinomas, 6 benign prostatic epithelial samples, and 6 prostate cell lines were sequenced on an Illumina GA II Sequencer. Paired-end sequencing was performed, reads were mapped to human genome (hg18) using ELAND alignment software. Gene expression was quantified using RSEQtools (available from the GERSTEIN RSEQtools web site). A full description of the PCA cases was reported in Pflueger et al. (PFLUEGER et al., Genome Res., 21:56-67 (2011)). Tumor DNA together with paired blood DNA was extracted from high density foci and areas of genomic gain and loss were assessed using the Affymetrix 6.0 SNP array platform.

Immunohistochemistry (IHC) and Fluorescent In Situ Hybridization (FISH). Validation studies were performed on 169 primary PCA, 37 NEPC, 22 benign formalin fixed, paraffin embedded prostate tissue samples using IHC for protein expression and FISH for gene amplification or ERG gene rearrangement. IHC was considered positive if >1% of tumor cells displayed immunoreactivity in cell cytoplasm (Aurora kinase A) or nucleus (Aurora kinase B, ERG). ERG rearrangement was assessed using dual-color break-apart interphase FISH assay as described previously (TOMLINS et al., Science; 310:644-8 (2005)); Tung et al., Prostate 71(7):675-81 (2011), Epub Oct. 14, 2010). In cases where FISH did not work, the TMPRSS2-ERG gene fusion was evaluated using reverse transcriptase PCR to screen for fusion transcript expression (as described in TOMLINS et al., Science, 310:644-8 (2005)).

Statistical Analysis. Wilcoxon test was applied for mRNA differential analysis, followed by Benjamini-Hochberg correction for multiple hypothesis testing. Pearson correlation and Fisher Exact test were implemented for gene-gene expression correlation and genomic aberration association analysis, respectively. T test method was used to determine differences in tumor volumes in xenograft studies, with criteria for significance <0.05.

Transfection, Quantitiative PCR, Immunoblot Analysis. Functional studies were performed using NCI-H660 cell line as a model of NEPC, and VCaP and LNCaP as models of PCA. All cell lines were purchased from ATCC (Manassas, Va.), and the 293FT cell line was purchased from Invitrogen (Carlsbad, Calif.) and maintained according to the manufacturers' protocols.

Drug Treatment. PHA-739358 was obtained from Nerviano Medical Sciences (Milan, Italy) in powder form (MW 414.36). Prostate cell lines for this study were obtained from the American Type Culture Collection (Manassas, Va.). RWPE ($20\times10^3$ per well), NCI-H660 ($20\times10^3$), DU145 ($5\times10^3$ per well), VCaP ($20\times10^3$ per well) and LNCaP ($1.5\times10^4$ per well) cells were seeded on 96-well-tissue culture plates. At 24 hours, cell lines were treated with vehicle (0.5% DMSO) or escalating doses of PHA-739358 (5 nM, 50 nM, 100 nM, 500 nM, 1 uM, 5 uM). At 48 hr, 72 h, 96 h, and 120 h, viability was assessed by performing WST-1 assay (Roche, Indianapolis, Ind.) reading absorbance at 450 nm according to the manufacturer's instructions. Xenografts were prepared by injection of 1 million NCI-H660 cells, VCaP cells, or LNCaP cells into NU/J mice (Jackson Laboratories, Bar Harbor, Me.). LTL-362 xenografts were established at BC Cancer Center Living Tumor Laboratory as previously described (TUNG et al., Prostate (2010)). 3×3×2 mm2 tissue fragments were subcutaneously engrafted into fourteen 6-8 week old NOD/SCID mice. All xenograft tumors were allowed to grow to an average tumor weight of 100 mm$^3$. 20 LNCaP, 20 VCaP, 40 NCI-H660, 14 LTL-362 mice were randomized to treatment with PHA-739358 at 30 mg/kg intraperitoneal dosing on days 1-5 or vehicle. Body weight, tumor volume based on caliper measurements (0.5236×length×width) and luciferase imaging were performed every 3 or 4 days after treatment. Mice were sacrificed on day 17, and tumors were evaluated for weight, gross pathology, histology, and IHC. Three tumors were processed during treatment (on day 4) to evaluate for phosphorylated histone 3 expression by IHC.

RNA-Sequencing (RNA-Seq). RNA was prepared for RNA-Seq using the Illumina Genome Analyzer II as detailed in the manufacturer's instructions. mRNA was isolated from frozen tissue using Trizol (Invitrogen, Carlsbad, Calif.). Total RNA was prepared in accordance with Illumina's sample preparation protocol for paired end (PE) sequencing of mRNA unless described otherwise. In brief, 5-10 ug of total RNA was fragmented by heat during 2.5 minutes, reverse transcribed and transformed to double stranded cDNA by reverse transcription using Superscript 2 Double-Stranded cDNA Synthesis kit (Invitrogen, USA) and random hexamer primers (Invitrogen). The inventors also integrated the use of T4 ligase (Enzymatics Inc., Beverly, Mass.) to improve the efficiency of adapter ligation. The gel dissolutions of all gel-based purification steps were conducted at room temperature under slight agitation as described by Quail et al. (QUAIL et al., Nat Methods, 5:1005-10 (2008)). After the enrichment of cDNA template by PCR, the concentrations and the sizes of the libraries were measured using DNA 1000 Kit (Agilent Technologies, Santa Clara, Calif.) on Agilent 2100 Bioanalyzer respectively. PE RNA- Seq was performed with the Genome Analyzer H (Illumina, San Diego, Calif.) generating PE reads of 54 bp. PE reads were then processed and mapped to the reference human genome (hg18) using ELAND alignment software. Gene expression was quantified by using RSEQtools (HABEGGER et al., *Bioinformatics*, 27:281-3 (2011)). Briefly, reads mapped on exonic regions were considered to computed gene expression via RPKM (reads per kilobase of exonic region per million reads) (MORTAZAVI A et al., *Nat Methods*, 5:621-8 (2008)). The inventors employed the UCSC known Gene annotation set as gene model reference. To account for multiple transcripts, the inventors defined the composite model, i.e. the union of all exonic nucleotides.

Affymetrix Genome-Wide Human SNP Array 6.0. High quality DNA was extracted from tumor tissue as well as peripheral blood mononuclear cells (when available), using the Qiagen DNA extraction kit per manufacturers instructions. DNA quality and quantity were evaluated by electrophoresis and Nanodrop (NanoDrop Technologies, Wilmington, Del.) spectrophotometer. The 6.0 SNP arrays were run at the Cornell University Microarray Core facility in Ithaca, N.Y. and assessed for focal and broad areas of genomic gain and loss per sample and across samples.

Immunohistochemistry (IHC). Formalin fixed paraffin embedded (FFPE) tissue sections were de-paraffinized and endogenous peroxidase was inactivated. Antigen retrieval was accomplished by heat/pressure cook for 10 minutes (Aurora-A), and using the Bond Epitope Retrieval Solution 1 (ER1) at 99-100° C. for 30 minutes (Leica Microsystems) for the other three antibodies. Following retrieval, the sections were incubated sequentially with the primary antibody for 25 minutes, post-primary for 15 minutes and polymer for 25 minutes ending with colorimetric development with diaminobenzidine (DAB) for 10 minutes (Bond Polymer Refine Detection; Leica Microsystems). Antibodies used were: Abcam ab13824, dilution 1:800 (Aurora kinase A), Abcam ab14955, dilution 1:2000 (Histone H3 phospho S 10), Epitomics 28051, dilution 1:100 (ERG). IHC was quantified on scale 0-3 and overexpression was defined as any staining intensity seen of target cells above background (similar methodology as was used in PARK et al., *Neoplasia*, 12:590-8 (2010)).

Fluorescent In Situ Hybridization (FISH). Interphase nuclei were evaluated for AURKA or MYCN amplification and ERG rearrangement using the following BAC clones: AURKA (RP 11-158017), MYCN (RP11-635A14), ERG (RP11-24 µl (red) and RP11-372017 (green)). Reference probe used when assessing AURKA and MYCN was located at 10q25 and was BAC RP11431P18, spanning a stable region of the chromosome. AURKA and MYCN were evaluated using Flourescence microscope (Olympus BX51). Amplification was defined as the presence 3 to 4 copies on average for gene-specific (i.e. AURKA or N-MYC) signals per nuclei compared to two reference signals. At least 100 nuclei were evaluated per core/tissue section. ERG rearrangement was assessed using dual-color break-apart interphase FISH assay as described previously (TOMLINS et al., *Science*, 310:644-8 (2005); Perner et al., *Cancer Res.* 66:8337-41 (2006)), which involves labeling two probes that span the telomeric and centromeric neighboring regions of the ERG locus: A nucleus that lacks ERG rearrangement demonstrates two pairs of juxtaposed red and green signals (which can form yellow signals). A nucleus with ERG rearrangement shows either split of one red-green (yellow) signal pair (indicating rearrangement through insertion), or one single red signal for the rearranged allele (indicating rearrangement through deletion). Frozen cases or unevaluable cases were evaluated for TMPRSS2-ERG gene fusion using reverse transcriptase PCR to screen for fusion transcript expression (as described in TOMLINS et al., *Science*, 310:644-8 (2005)).

Transfection. Transient transfections of Aurora kinase A and N-myc were performed using Lipofectamine 2000 (Invitrogen) according to the manufacturers' instructions (plasmids kindly provided by Dr Steffi Herold, Theodor-Boveri-Institute, Biocenter. Am Hubland). siRNA transfection was performed using 60 nM AURKA siRNA (ON-TARGETplus SMARTpool L-003545-01-0005, Human AURKA, NM_198437; Thermo Scientific, Waltham, Mass.) or 100 nM control nonsilencing siRNA (ON-TARGETplus Non-targeting Pool D-001810; Thermo Scientific, Waltham, Mass.). siRNA was introduced into cells using Minis TransIT-TKO transfection reagent were performed following the manufacturer's protocol. Briefly $10^5$ NCI-H660 cells were seeded in 12-wells in 1 mL medium and transfected with siRNA targeting AURKA mRNA or scrambled siRNA as a negative control. Following 48 hours RNA was extracted and quantitative RT-PCR was performed. All experiments were performed in duplicate. The inventors used the pBABE vector (kind gift of Dr. William Hahn at the Broad Institute and the Dana Farber Cancer Center) to generate stable LNCaP cells expressing N-myc. The retroviral construct was transfected into 293FT cells with Lipofectamine 2000 (Invitrogen, Carlsbad, Calif.) according to the manufacturer's instructions. The virus was harvested 72 hours later and used to infect LNCaP cells. Selection was carried out with 1 ug/mL Puromycin. For virus-induced knock-down of AURKA mRNA in NCI-H660 cells, pLKO.1 vectors containing short hairpin(sh) Aurora A were purchased from Openbiosystems and viral particles were packaged by co-transfecting HEK 293 FT cells with pLKO.1-sh-Aurora A, delta 8.9 and VSV-G plasmids. Viral supernatant was collected, filtered through 0.45 µl filter and concentrated using Lenti-X-Concentrator (Clontech). NCI-H660 cells were plated in 6 well plates and transduced with lentivirus containing sh-Aurora A or GFP.

Quantitative PCR. Quantitative PCR was performed using SYBR Green dye on Applied Biosystems 7500 Real Time PCR system (Applied Biosystems, Foster City, Calif.). The primer sequences for AURKA were GCCCTGTCTTACT-GTCATTCG (SEQ ID NO: 1) (forward) and AGAGAGTG-GTCCTCCTGGAAG (SEQ ID NO: 2) (reverse). Primers for MYCN were CTGGGAACTGTGTTGGAG (SEQ ID NO: 3) (forward) and CGACTGAGGGCTTCTTTC (SEQ ID NO: 4) (reverse). Primers for NSE were CTG-GCTAAATACAACCAGCTCA (SEQ ID NO: 5) (forward) and CACAGCACACTGGGATTACG (SEQ ID NO: 6) (reverse). All primers were designed using Beacon Designer and purchased from Invitrogen.

Immunoblot Analysis. Protein lysates were prepared in the RIPA buffer (radioimmunoprecipitation assay lysis buffer) supplemented with protease inhibitor cocktail and phosphatase inhibitors (Thermo Scientific, Waltham, Mass.). The total protein concentration of the soluble extract was determined using the BCA protein assay Kit (Thermo Scientific). Each protein sample (30 ug) was resolved to SDS-PAGE, transferred onto a polyvinylidene difluoride membrane (Millipore) and incubated overnight at 4° C. with primary antibodies. The antibodies used were: Abcam ab1287 (Aurora kinase A), Santa Cruz sc53993 (B8.4.B,N-Myc), Upstate biotechnology 05-806 (histone H3 phospho S10), Cell Signaling 4329 (synaptophysin), Millipore MAB324 (NSE), Cell Signaling #2914S (phospho-Aurora A (Thr288)/Aurora B (Thr232)/Aurora C (Thr198)), Epitomics, #1805-1

(Aurora-C), Abcam, #ab2254 (Aurora-B) and Epitomics, #2251-1 (GAPDH). Following three washes with TBS-T, the blot was incubated with horseradish peroxidase-conjugated secondary antibody and immune complexes were visualized by enhanced chemiluminescence detection (ECL plus kit, GE Healthcare, UK). The blot was reprobed with monoclonal antibody against beta-actin (Sigma). Total protein was extracted and separated by gel electrophoresis. Protein was then transferred to nitrocellulose membranes and probed overnight using the appropriate primary antibodies.

Co-Immunopreciptiation. Cell lysates were prepared by lysing cells in buffer containing 50 mM Tris (pH 7.5), 120 mM NaCl, 0.5% NP-40, 5 mM EDTA and protease and phosphatase inhibitors (Thermo Scientific), followed by sonication. 500 ug of total protein extract was incubated with 1 ug of anti N-Myc or control IgG overnight. Antigen-antibody complexes were pulled down using Protein A conjugated agarose bead (Roche Applied Science) and washed 5 times using lysis buffer.

Protein Stability. Cells were treated with 50 ug of cycloheximide (Sigma-Aldrich) for indicated times and lysed in 50 mM Tris (pH 8.0), 150 mM NaCl, 1% NP-40 and protease inhibitors. Proteins were separated in SDS-PAGE, transferred to PVDF membrane and blotted with anti N-Myc (1:1,000, Santa Cruz Biotechnology) or anti Aurora A (1:1, 000, Cell Signaling). Protein loading was determined by stripping blotted membrane using Restore PLUS buffer (Thermo Scientific) and blotting with anti alpha-Tubulin antibodies (1:5,000, Epitomics). Normalized percent of Aurora kinase A was calculated from the immunoblot by dividing the intensity of each Aurora A band by that of beta-tubulin and then dividing this ratio from that calculated for 0 time point.). Bands were quantified using Versadoc Imaging System (BioRad) and QuantityOne (BioRad) software.

Chromatin Immunoprecipitation. For the ChIP assays we followed the procedure from a previous publication (RICKMAN et al., Neoplasia, 12:1031-40 (2010)). Briefly, the inventors used MatInspector (version 8.0; Genomatix Software GmbH, Munich) (8) to identify N-myc binding sites in the promoter regions of NSE (864 base pairs) and SYP (721 base pairs) and AR (760 base pairs) of genomic sequence near the respective transcription start sites in silico. Briefly, 50×10$^6$ LNCaP_nMyc or LNCaP_EV (empty vector control) cells were washed in PBS twice and then fixed using 1% formaldehyde for 10 minutes at room temperature and quenched using 125 mM glycine. The cells were centrifuged and the cell pellet was resuspended in 2 milliliters of dilution buffer (165 mM NaCl, 0.01% SDS. 1.1% Triton X-100, 1.2 mM EDTA pH 8.0, 16.7 mM Tris HCl pH8.0, 1 mM PMSF). Protein-bound chromatin was fragmented by sonication for 10 minutes (cycles of 30 seconds pulses of sonication followed by 30 seconds of rest). Equal volumes of chromatin were immunoprecipitated with either mouse anti-N-Myc (Santa Cruz sc53993 (B8.4.B,N-Myc) or mouse IgG (Santa Cruz sc2025) as a negative control. Following extensive washing the DNA was eluted using 100 mM NaHCO3 and 1% SDS and the crosslinks were reversed using 300 mM NaCl at 65° C. for 16 hours. The eluted DNA was purified using Qiagen PCR Qiaquick kit following manufacturer's protocol. For qPCR amplification the inventors used the ABI 7500fast system and the relative standard curve method in a 96-well format. For this, the inventors designed primer sets that target each of the E-boxes mapped to the promoter regions (Table 3). Two microliters of either eluted DNA or a 1:10 dilution of the input chromatin preparation from each cell line was assayed in order to calculate the percentage of enrichment. Primers targeting a copy number stable chromosomal region in ARHGEF11 (chr1:55205397-155205600, hg18) were used as a negative control as previously described (RICKMAN et al., Cancer Res., 69:2734-8 (2009)). Input DNA was also analyzed at 5 concentrations (0.004 ng-40 ng) to generate the standard curve per primer pair and per 96-well plate. All reactions were run in triplicates.

Cell Cycle Analysis. Cells were treated with PHA-739358 for 48 hrs. After treatment, cells were washed with cold PBS and fixed in 70% EtOH at −20° C. overnight. Cells were washed and suspended in 500 µl PBS containing 0.1% Triton X-100, 20 µg/ml Propidium Iodide (PI) and 200 µg/ml RNase A, incubated for 30 min at room temperature and subjected to FACS analysis using a LSR II Analyzer (BD Biosciences).

TABLE 3

Primer sets that target E-boxes mapped to the promoter regions.

| Name | Sequence | SEQ ID NO: |
|---|---|---|
| TERT_ChIP f | CAGTGGATTCGCGGGCACAGA | 7 |
| TERT_ChIP r | AAGGTGAAGGGGCAGGACGGG | 8 |
| SYP_ChIP Ebox1f | TTGTGTTTTCCCAACGCATATTCC | 9 |
| SYP_ChIP Ebox1r | AGCGGGTTGTACCACAGTCTC | 10 |
| SYP_ChIP Ebox2f | CCTGGGCTGTTCCAACGAG | 11 |
| SYP_ChIP Ebox2r | GCTCTGTCCACGGTGCTG | 12 |
| NSE_ChIP Ebox1 | CGGTCCTCTGGGCAGTGTG | 13 |
| NSE_ChIP Ebox1 | AGCCGCCTTCGCAAGTCTC | 14 |
| NSE_ChIP Ebox 2 and 3 f | CCGCCGCCACTGCCACTC | 15 |
| NSE_ChIP Ebox 2 and 3 r | GGGCTTCACCTCGGGACTGC | 16 |

Xenografts. 1 million NCI-H660 cells, VCaP cells, or LNCaP cells were injected into NU/J mice (Jackson Laboratories, Bar Harbor, Me.). LTL-362 xenografts were established at BC Cancer Center Living Tumor Laboratory as previously described (Tung et al. (2010), supra), and 3×3×2 mm2 tissue fragments were subcutaneously engrafted into fourteen 6-8 week old NOD/SCID mice. Three different studies were performed comparing the effect of PHA-739358 on tumor growth of NCI-H660 and LNCaP xenograft tumors (study 1), NCI-H660 and VCaP xenografts (study 2), and LT-362 xenografts (study 3). Study 3 was conducted at University of British Columbia BC Cancer Center. Tumors were allowed to grow to an average tumor weight of 100 mm$^3$. For each study 14-20 mice bearing tumors from each cell type were randomized to treatment with PHA-739358 (Nerviano Medical Sciences, Milan, Italy) at 30 mg/kg intraperitoneal dosing on days 1-5 or vehicle. Body weight, tumor volume based on caliper measurements (0.5236×length×width) and luciferase imaging were performed every 3 or 4 days after treatment. Mice were sacrificed on day 17, and tumors were evaluated for weight, gross pathology, histology, and IHC. 3 tumors were processed during treatment (on day 4) to evaluate for phosphorylated histone 3 expression by IHC. In order to image viable tumor cells optimize tumor volume measurements we injected VCaP with retrovirus particles containing the sgfn-TGL triple reporter vector as previously described (PONOMAREV et al., *Eur J Nucl Med Mol Imaging*, 31:740-51 (2004). LNCaP and NCI-H660 cells were engineered to express luciferase using a transposable element vector (kind gift from John Ohlfest, University of Minnesota Medical School, Minneapolis, Minn.) as described previously (Wu et al., *Cancer Gene Ther.* 14:550-60 (2007)). On the day of imaging, (intraperitoneal) 100-microliters of D-Luciferin (75 mg/kg) were injected into anesthetized mice. Ten minutes later the mice animals were placed on their ventral side and bioluminescence images were acquired with the IVIS Imaging System (Xenogen). Analysis was performed using LivingImage software (Xenogen) by measurement of the average photon flux (measured in photons/s/cm2/steradian) within a region of interest.

EXAMPLE 2

In this Example, the inventors examined the histological spectrum of t-NEPC and evaluated AURKA and MYCN amplification in primary prostate tumors and metastases from 72 patients who developed lethal t-NEPC. The inventors identified three morphologic groups of t-NEPC consisting of pure neuroendocrine carcinoma, which included small cell and large cell neuroendocrine carcinoma, poorly differentiated adenocarcinoma with or without neuroendocrine differentiation, and mixed tumors. Amplification of AURKA was identified in 64% of evaluable primary PCa (treated and hormone naïve) from patients with t-NEPC, and in 92% of metastases; of these cases, 69% of primary PCa and 82% of metastases also harbored concurrent amplification of the N-myc gene (MYCN). In contrast, in an unselected PCa cohort, AURKA and MYCN amplifications were identified in only 6% of 172 cases. Interestingly, 3/3 cases of PCa with Paneth cell-like neuroendocrine differentiation in the unselected cohort harbored AURKA amplification, one of which also had MYCN amplification. When metastatic t-NEPC was compared to primary PCa in same patient, there was 100% concordance of ERG rearrangement, 100% concordance of AURKA amplification and 60% concordance of MYCN amplification. In prostate tumors with mixed features, there was also 100% concordance of ERG rearrangement and 94% concordance of AURKA and MYCN co-amplification between areas of t-NEPC and adenocarcinoma. AURKA and MYCN amplifications were not present in benign prostate tissue.

Results

Figure 6:
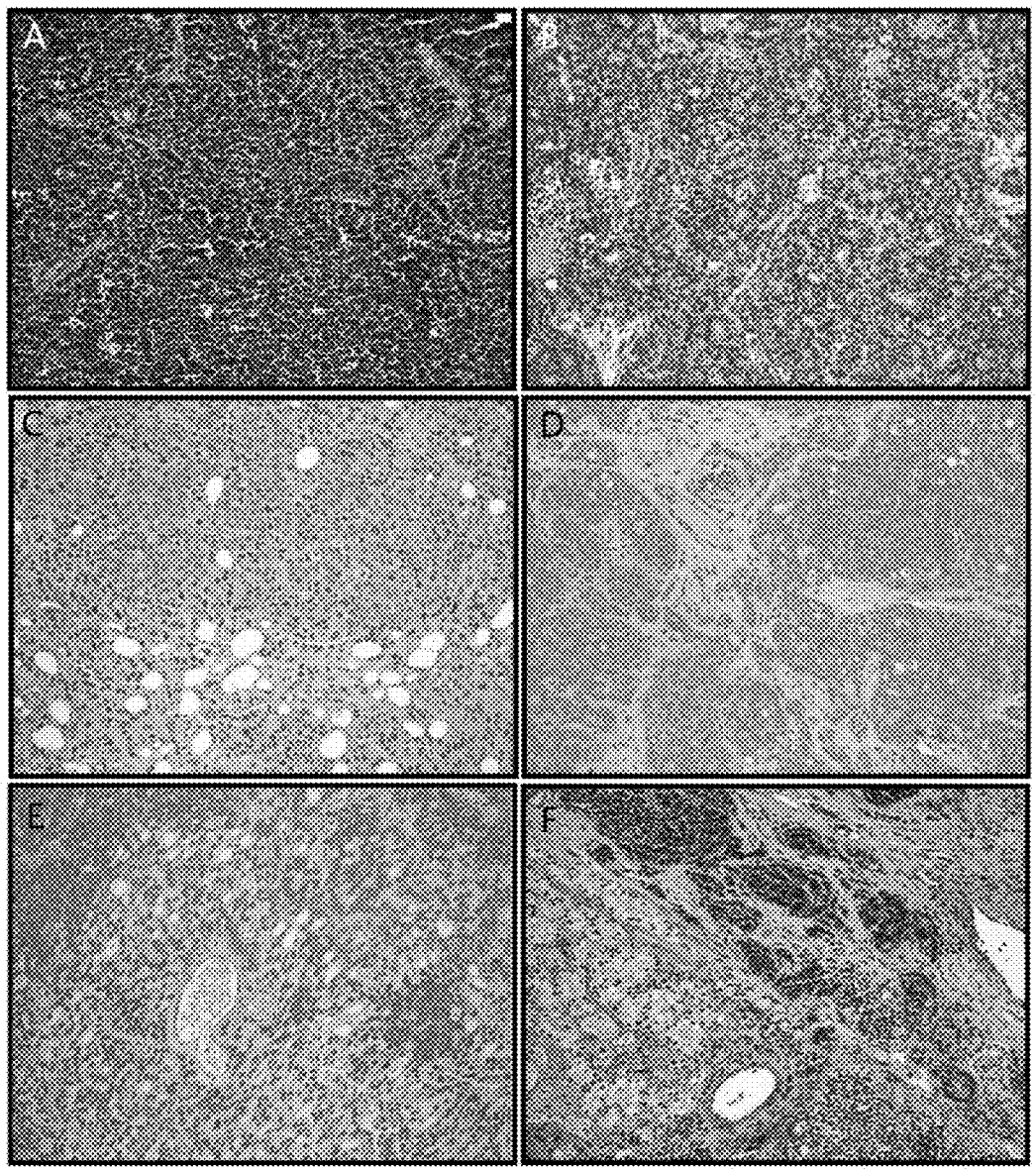
FIG. 6. Morphological spectrum of treatment-related neuroendocrine prostate cancer (t-NEPC). A) Small cell carcinoma of the prostate. The tumor is composed of sheets of uniform cells with scant cytoplasm, hyperchromatic nuclei, coarse chromatin, and unapparent nucleoli. B) Large cell neuroendocrine carcinoma of the prostate. Tumor is composed of sheets and ribbons of cells with abundant cytoplasm, large nuclei with coarse chromatin, brisk mitotic activity and foci of necrosis; pseudorosettes are also apparent. C) Metastatic poorly differentiated adenocarcinoma of the prostate without neuroendocrine differentiation, treated (metastatic castration-resistant prostate cancer). Sheets of tumor cells with pale eosinophilic cytoplasm and abundant mitotic figures are seen within fibroadipose tissue. D) Poorly differentiated adenocarcinoma of the prostate with neuroendocrine differentiation, treated (castration-resistant prostate cancer). Note the vaguely organoid pattern of tumor cells, which have amphophilic cytoplasm and prominent nucleoli. E) Poorly differentiated adenocarcinoma of the prostate with focal areas of neuroendocrine differentiation, treated (castration-resistant prostate cancer). Tumor cells with neuroendocrine differentiation are interspersed and demonstrate basophilic appearance. F) Mixed t-NEPC and adenocarcinoma of prostate, treated (castration-resistant prostate cancer). Areas of small cell carcinoma and poorly differentiated adenocarcinoma are seen. H&E stain, original magnification 20×.

Histopathology. Microscopic evaluation of 52 treated PCa cases and 12 metastases demonstrated three major histologic groups: a) Pure neuroendocrine prostate carcinoma, which included small cell carcinoma (n=18) and large cell neuroendocrine carcinoma (n=1); b) poorly differentiated adenocarcinoma with (n=21) or without (n=6) neuroendocrine differentiation; c) mixed neuroendocrine carcinoma and adenocarcinoma (n=18). Among the latter group of 18 cases with mixed morphology, the neuroendocrine carcinoma component included areas of small cell carcinoma (n=15) and large cell neuroendocrine carcinoma (n=3) (FIG. 6).

The prostate specimens from two patients who developed neuroendocrine prostate cancer de novo corresponded to one case of mixed small cell carcinoma with areas of PCa Gleason score 5+4=9 (prostate needle biopsies), and one case of mixed large cell neuroendocrine carcinoma with areas of PCa with ductal features (transurethral resection of prostate).

FISH Results. In the group of primary hormone naïve PCa cases from patients who clinically progressed to t-NEPC, AURKA amplification was identified in 11 of 17 (65%), 7 of which (64%) also had MYCN amplification. Among t-NEPC cases, AURKA amplification was identified in 29 of 46 (63%) assessable-treated PCa, and in 11 of 12 (92%) metastases. Concurrent MYCN amplification was present in 20 treated tumors (69%) and in 9 metastases (82%). In only two cases MYCN gain occurred in absence of AURKA amplification.

Figure 7:
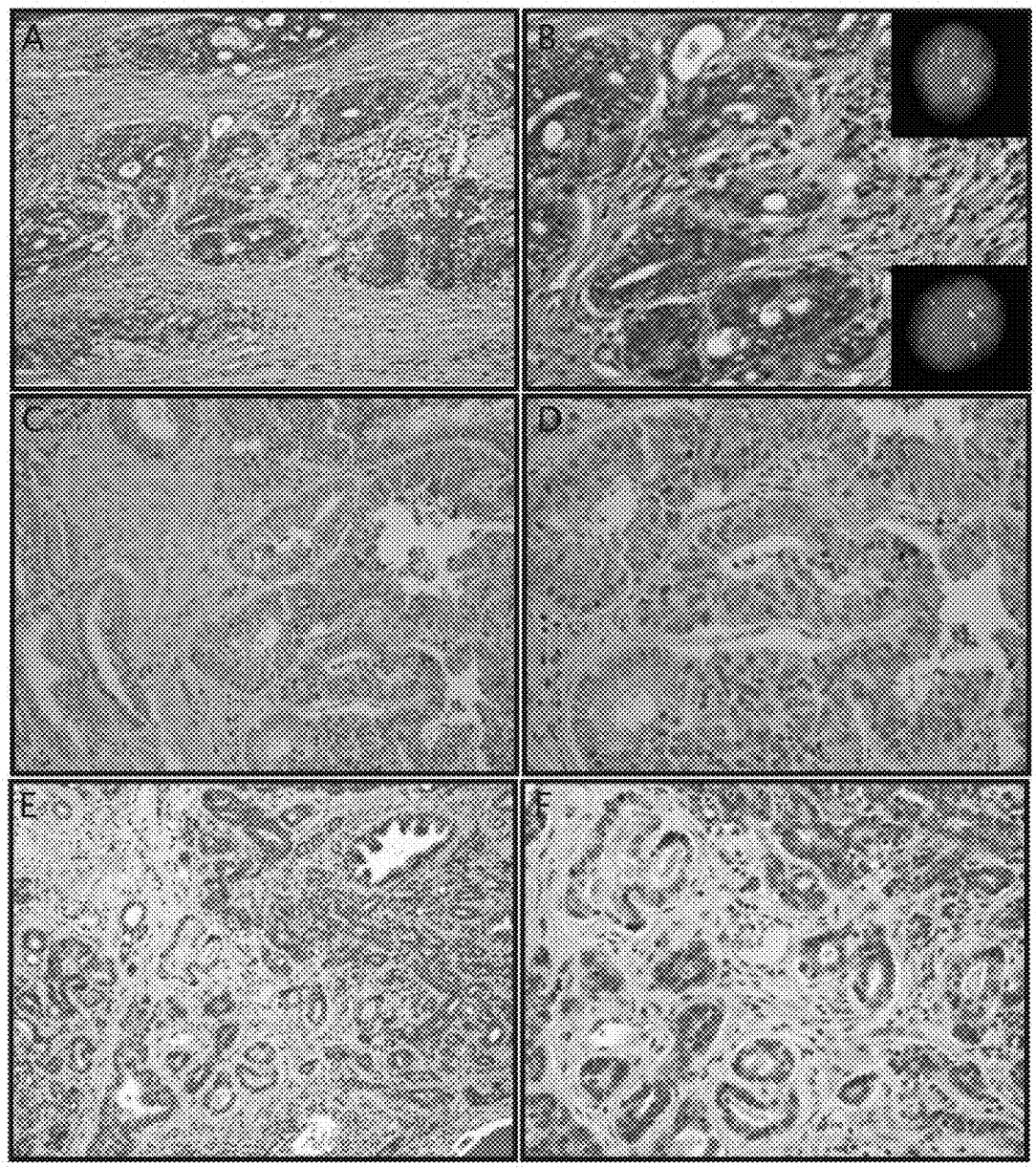
FIG. 7. Prostate cancer with Paneth cell-like neuroendocrine differentiation harbors AURKA and MYCN amplification. Three cases of localized prostate cancer with Paneth cell-like features were identified in the unselected cohort of tumors used as controls. At medium-power magnification (left side panels), cells with eosinophilic cytoplasm are easily identified. At high-power magnification (right side panels), tumor cells with Paneth-cell like neuroendocrine differentiation contain distinct large eosinophilic granules in the cytoplasm. One case (A and B) demonstrated AURKA and MYCN amplification and the other two cases (C and D; E and F) harbored AURKA amplification only (insets). H&E stain, original magnification 20×-left side panels and 40×-right side panels; FISH images, original magnification 60×.

In contrast, AURKA and MYCN amplifications were identified only in 6% of 172 cases of the unselected PCa cohort. Particularly noteworthy is the fact that AURKA amplification was detected in all three cases of PCa with Paneth cell-like neuroendocrine differentiation, one of them with concurrent MYCN amplification (FIG. 7). This particular histomorphology of PCa may be enriched for AURKA amplification, with resultant clinical implication for the diagnostician.

AURKA and MYCN amplification was detected in more than 95% of nuclei evaluated on each positive case. No AURKA or MYCN amplification was detected in benign prostate tissue (n=35).

Figure 8:
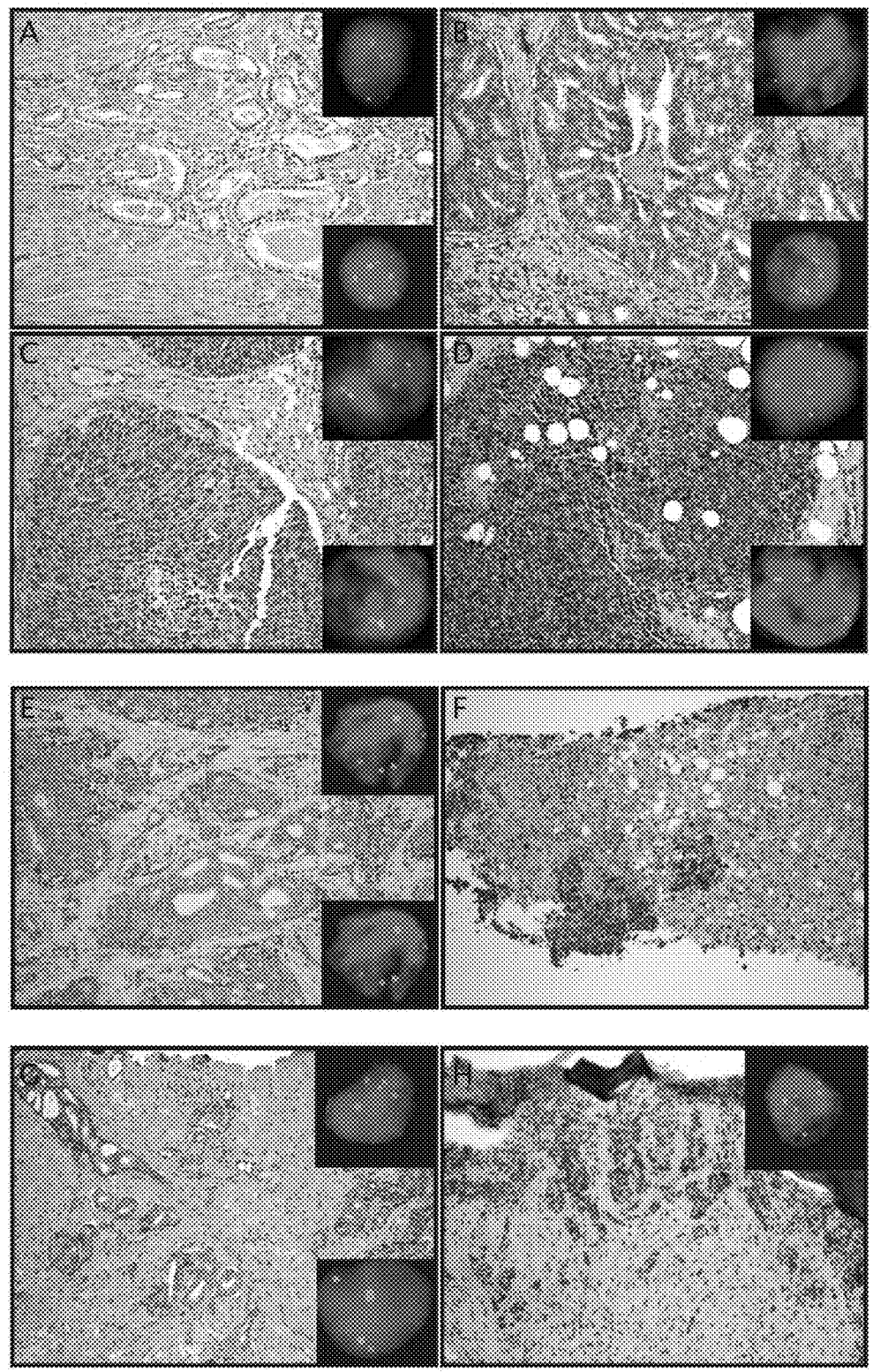
FIG. 8. AURKA and MYCN amplification in primary prostatic adenocarcinoma predicts the development of treatment-related neuroendocrine prostate cancer (t-NEPC). A-D) Top panel illustrates several specimens from a patient at different stages of disease progression to t-NEPC. A and B) Images of hormone naïve prostate cancer with areas of Gleason score 3+3=6 (A) and 4+5=9 (B) at initial diagnosis. Concurrent AURKA (upper inset) and MYCN (lower inset) amplification is present in both areas. C) Subsequent metastasis/local recurrence in the bladder demonstrates poorly differentiated adenocarcinoma without neuroendocrine differentiation, exhibiting both AURKA and MYCN amplification (upper and lower inset, respectively). D) Fiver years after treatment, patient presents with metastatic large cell neuroendocrine carcinoma in pelvic soft tissue. The tumor has organoid appearance focally forming pseudorosettes, and cells have abundant cytoplasm and prominent nucleoli. The tumor has both AURKA and MYCN amplification (upper and lower inset, respectively). Clonal origin is confirmed by ERG rearrangement through translocation in all tumors (pending image as inset). E-F) Center panel illustrates prostatectomy specimen from a patient with initial diagnosis of prostate adenocarcinoma Gleason score 4+5=9 (E), which has concurrent AURKA and MYCN amplification (upper and lower inset, respectively). A liver biopsy 7 years after (F) shows metastatic small cell carcinoma, which harbors AURKA and MYCN co-amplification as well. Clonal origin is confirmed by ERG rearrangement through deletion in both tumors. G-H) Lower panel illustrates needle biopsies from a patient with initial diagnosis of prostate adenocarcinoma Gleason score 4+3=7 (G) with amplification of AURKA and MYCN (upper and lower inset, respectively). Eight years after initial diagnosis and intermittent treatment, patient developed pancytopenia and bone lytic lesions, which biopsy (H) demonstrates metastatic small cell carcinoma (frozen tissue artifact present), consistent with spread from known prostatic primary. In addition to AURKA and MYCN co-amplification (upper and lower inset, respectively), clonal origin is confirmed by ERG rearrangement through translocation in both tumors. H&E stain, original magnification 20×; FISH images, original magnification 60×.
Figure 9:
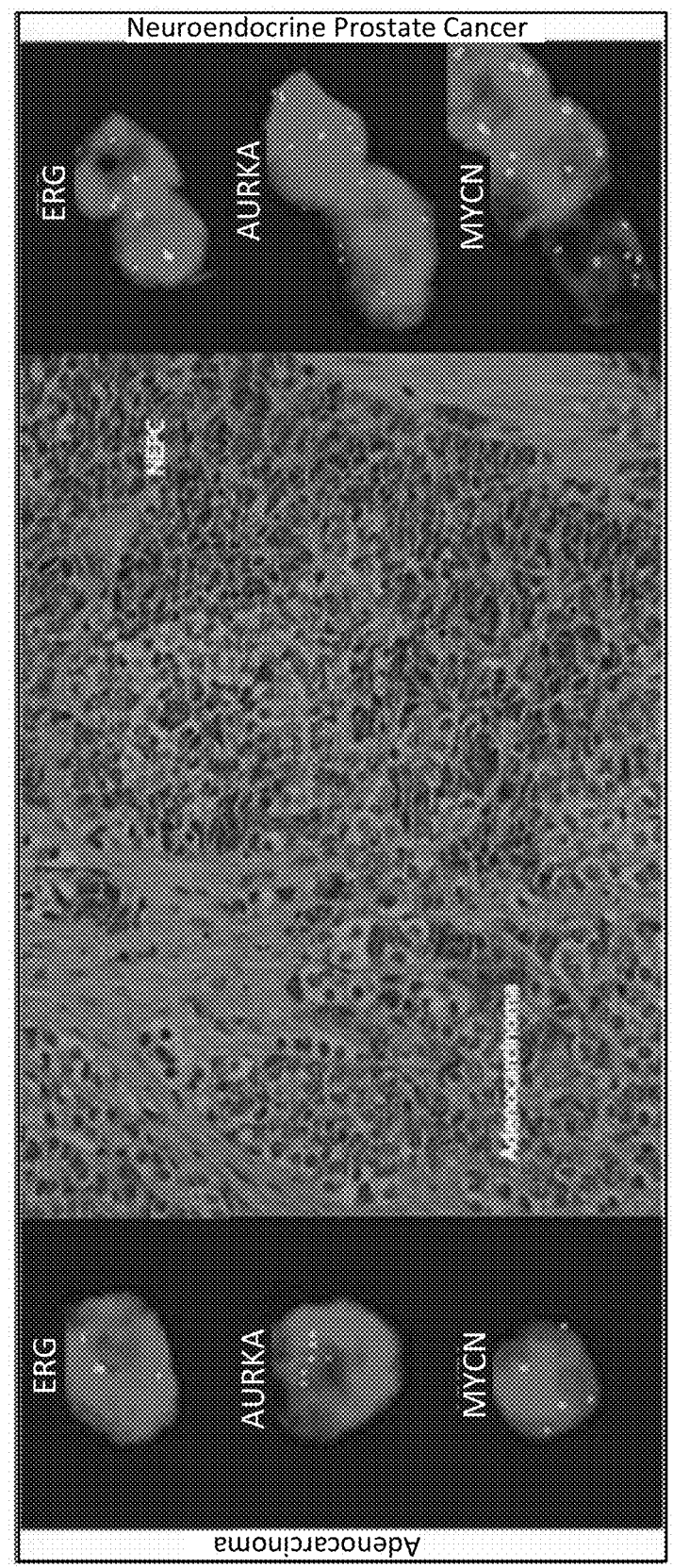
FIG. 9. Concordance of AURKA and MYCN amplification in tumors with mixed areas of neuroendocrine carcinoma and poorly differentiated adenocarcinoma. Representative image of local recurrence of castration-resistant prostatic carcinoma with mixed areas of small cell carcinoma (right) and adenocarcinoma (left). Both areas demonstrate concordance of AURKA and MYCN amplification. Clonal origin is supported by ERG rearrangement through translocation in both areas. H&E stain, original magnification 20×; FISH images, original magnification 60×.

In the 5 cases where metastatic t-NEPC was compared to primary PCa from the same patient, either hormone naïve or treated PCa, there was 100% and 60% concordance of AURKA and MYCN amplification, respectively. Histological and molecular findings of three of these cases are illustrated herein (FIG. 8). In prostate tumors with mixed features, there was 94% concordance between areas of neuroendocrine carcinoma and adenocarcinoma (FIG. 9).

Overall, ERG rearrangement was observed in 28 of 68 (41%) assessable tumors in this study, 9 through insertion and 19 through deletion. PTEN deletion was observed in 14 of 48 (29%) assessable cases, 8 of which were also ERG rearranged. Among the 5 cases of metastatic t-NEPC with matching PCa (hormone naïve or treated), four were positive for ERG rearrangement in the PCa and corresponding metastases, and one was negative for such gene rearrangement in both sites. This 100% concordance of ERG rearrangement supports clonal origin of t-NEPC, identical to those findings observed in tumors with mixed features.

In neuroendocrine tumors from non-prostate origin, AURKA amplification was detected in 10 of 11 (91%) assessable small cell carcinomas from lung and bladder, including the metastasis to cerebellum. MYCN amplification was detected in 7 of these cases, always in the presence of AURKA amplification. In contrast, AURKA/MYCN amplifications were not seen in well-differentiated neuroendocrine tumor ('typical carcinoid') of bowel and metastases, or in DCIS with neuroendocrine differentiation (not shown).

Materials and Methods

Case Selection. Pathology material from 72 patients who clinically developed neuroendocrine prostate cancer was evaluated. Cases were identified at different collaborating institutions under IRB-approved protocols for the purpose of this study. Clinical parameters for diagnosis of t-NEPC included rapid progression of the disease with visceral and/or lytic bone metastases, normal or slightly elevated PSA (≤10 ng/ml), and elevated neuroendocrine serum markers (Chromogranin A, NSE). With exception of two cases (patients who developed neuroendocrine prostate cancer de novo), patients received androgen deprivation therapy before disease progression toward t-NEPC.

Clinical information was available in 32 of 72 patients including the age at diagnosis of PCa, clinical stage, type of primary and systemic therapy, interval of time between initial diagnosis and castration-resistant state, interval of time between castration-resistant prostate cancer (CRPC) and metastatic disease and death.

The age at diagnosis of PCa ranged from 42 to 84 years (median=65 years). Time interval to progression to CRPC ranged from 2 to 10 years (median=4 years), and overall survival after clinical diagnosis of NEPC ranged from 8 to 14 months (median=12 months).

An unselected cohort of 172-localized PCa was used as control. The age at diagnosis of PCa in this cohort ranged from 42 to 75 years (median=62 years).

Pathologic Evaluation. Formalin-fixed paraffin embedded (FFPE) tissue from different specimens of the aforementioned cases was available. Hematoxylin and Eosin (H&E)-stained slides from surgical resections and biopsies were reviewed by study pathologists. Pathologic evaluation included Gleason score of (untreated) tumors based on prostate biopsy and/or prostatectomy specimens, tumor stage, and histological examination of metastases and treated prostate tumors.

Archival tissue from the 72 patients who developed t-NEPC included 13 primary hormone naïve PCa cases only (matched treated PCa or metastasis unavailable), 49 treated PCa only (matched hormone naïve PCa or metastasis unavailable), 1 case of hormone naïve PCa with available tissue of treated PCa and metastases, 3 cases of hormone naïve PCa and subsequent metastases after treatment (matched treated PCa unavailable), 1 treated PCa and subsequent metastases (matched hormone naïve PCa unavailable), and 5 cases of metastases only (matched hormone naïve or treated PCa unavailable). Sites of visceral metastases included retroperitoneum, colon, bladder, brain, pleura, pelvic soft tissue, epidural soft tissue, and liver.

Overall pathology material from these 72 patients at different stages of the disease included 17-hormone naïve PCas, 52 treated PCa and 12 metastases, some with multiple specimens. The Gleason score of the 17 hormone naïve PCa ranged from 3+3=6 to 5+5=10, and their pathologic tumor stage ranged from pT2c NO to pT3a N1.

The Gleason score of the 172 cases of localized PCa used as controls ranged from 3+3=6 to 4+5=9, and their pathologic tumor stage ranged from pT2a to pT3b. Three cases of PCa with Paneth cell-like neuroendocrine differentiation were identified and their corresponding Gleason scores were 3+4=7, 4+3=7 and 4+5=9. Archival material from this control cohort also included 35 benign prostate tissue samples.

A subset of 19 neuroendocrine tumors from non-prostate origin was also interrogated for AURKA and MYCN amplification and included small cell carcinoma of lung (n=12) and bladder (n=2), metastatic small cell carcinoma of lung to cerebellum (n=1), well-differentiated neuroendocrine tumor ('typical carcinoid') of bowel (n=1), metastatic well-differentiated neuroendocrine tumor ('typical carcinoid') of bowel to liver (n=1) and lung (n=1), and mammary ductal carcinoma in situ (DCIS) with neuroendocrine differentiation (n=1).

Fluorescence In Situ Hybridization (FISH). To assess AURKA and MYCN amplification, and PTEN status, the inventors used a locus specific probe plus reference probe FISH assays as described in Example 1 and by BERGER et al., *Nature*, 470(7333):214-220 (2011). Amplification was defined as the presence of 4 or more copies on average for gene-specific (AURKA or MYCN) signals per nucleus compared to two reference signals. ERG rearrangement was assessed using dual-color break-apart interphase FISH assay as described previously (TOMLINS et al., *Science*, 310 (5748): 644-648 (2005); PERNER et al., *Cancer Res*, 66(17): 8337-8341 (2006)). At least 100 nuclei were evaluated per tissue section using a fluorescence microscope (Olympus BX51; Olympus Optical, Tokyo, Japan).

Immunohistochemistry (IHC). IHC stain was performed in a subset of 44 cases using antibodies for Synaptophysin (Clone SP11 from Lab Vision/Thermo Fisher Scientific; Kalamazoo, Mich.), Chromogranin A (Clone LK2H10 from Biogenex; Fremont, Calif.) and Androgen Receptor (AR) (Clone F39.4.1 from Biogenex; Fremont, Calif.) following vendors' specified optimal dilutions for IHC. Poorly differentiated adenocarcinomas were considered to have neuroendocrine differentiation when more than 5% of tumor cells were positive for Synaptophysin or Chromogranin A.

---

What is claimed is:

1. A method of subtyping prostate cancer, comprising:
obtaining a biological sample containing prostate cancer cells from a human subject having prostate cancer,
detecting amplification of AURKA in the biological sample by a fluorescent in situ hybridization (FISH) assay,
subtyping the prostate cancer as neuroendocrine prostate cancer (NEPC) or likely to develop into NEPC based on presence of the amplification of AURKA in the biological sample; and
administering a small molecule Aurora A kinase inhibitor to the human subject for treating prostate cancer subtyped as having NEPC or likely to develop NEPC.

2. The method of claim 1, wherein said biological sample is a prostate tissue biopsy, urine, blood, semen, or prostatic secretions.

3. The method of claim 1, further comprising detecting ERG rearrangement.

4. The method of claim 3, wherein said ERG rearrangement is detected in a break-apart FISH assay.

5. The method of claim 1, wherein said human subject has not been subjected to hormone therapy.

6. The method of claim 1, wherein said human subject is undergoing hormone therapy.

7. The method of claim 1, wherein said small molecule Aurora A kinase inhibitor is selected from the group consisting of VX-680/MK-0457, PHA-739358, MLN8054, MLN8237, SNS-314CYC116, PF-3814735, ENMD2076, AT-9283, R-763/AS-703569, and AMG900.

8. The method of claim 1, wherein said amplification is determined based on a gain of at least one in the copy number of the AURKA gene.

9. The method of claim 8, wherein said gain of at least one in the copy number of the AURKA gene is determined based on detecting at least three fluorescent signals in an interphase nucleus using a fluorescently labeled nucleic acid probe specific for the AURKA gene.

* * * * *

UNITED STATES PATENT AND TRADEMARK OFFICE
CERTIFICATE OF CORRECTION

PATENT NO.        : 9,568,483 B2
APPLICATION NO.   : 14/112358
DATED             : February 14, 2017
INVENTOR(S)       : Mark A. Rubin et al.

It is certified that error appears in the above-identified patent and that said Letters Patent is hereby corrected as shown below:

In the Specification

Column 1, Line 14 should read:
STATEMENT REGARDING FEDERALLY SPONSORED RESEARCH OR DEVELOPMENT
This invention was made with Government support under Grant Number CA111275 awarded by the National Institutes of Health. The Government has certain rights in the invention.

Signed and Sealed this
Ninth Day of May, 2017

Michelle K. Lee
*Director of the United States Patent and Trademark Office*